United States Patent
Farkas

(10) Patent No.: US 9,772,061 B2
(45) Date of Patent: Sep. 26, 2017

(54) EXAMINATION PROCESS FOR THE IN SITU DETERMINATION OF RATE OF FEEDING AN INHIBITOR INTO A GAS PIPELINE FOR PREVENTING HYDRATE FORMATION

(71) Applicant: Pal Farkas, Totkomlos (HU)

(72) Inventor: Pal Farkas, Totkomlos (HU)

( * ) Notice: Subject to any disclaimer, the term of this patent is extended or adjusted under 35 U.S.C. 154(b) by 0 days.

(21) Appl. No.: 15/077,476

(22) Filed: Mar. 22, 2016

(65) Prior Publication Data

US 2017/0114941 A1    Apr. 27, 2017

Related U.S. Application Data

(63) Continuation-in-part of application No. 14/919,060, filed on Oct. 21, 2015, now abandoned.

(30) Foreign Application Priority Data

Nov. 24, 2015   (HU) ..................................... 1500554

(51) Int. Cl.
    *F16L 58/00*    (2006.01)
    *G05D 11/13*    (2006.01)
(52) U.S. Cl.
    CPC ............ *F16L 58/00* (2013.01); *G05D 11/135* (2013.01)
(58) Field of Classification Search
    CPC .................. A47B 43/00; F25J 1/00; F25J 3/00
    (Continued)

(56) References Cited

U.S. PATENT DOCUMENTS

| 4,456,067 A | * | 6/1984 | Pinner, Jr. | ................ | C09K 8/92 |
| | | | | | 166/279 |
| 4,474,591 A | * | 10/1984 | Arand | ...................... | C10G 5/00 |
| | | | | | 62/630 |

(Continued)

OTHER PUBLICATIONS

U.S. Appl. No. 14/919,060, Pal Farkas, Mar. 22, 2016.*

*Primary Examiner* — Jewel V Thompson
(74) *Attorney, Agent, or Firm* — Olson & Cepuritis, Ltd.

(57) ABSTRACT

The invention relates to an examination process for replicating hydrate forming conditions in a gas pipeline and monitoring the effect of a low dosage hydrate inhibitor (LDHI) in suppressing hydrate formation at temperatures encountered in gas pipelines for dynamically determining LDHI feed rate for inhibition of hydrate formation comprising the steps of:
  diverting from a gas well a sample gas stream at a preselected rate;
  introducing the diverted gas stream into a gas conduit through an inlet of the gas conduit;
  feeding LDHI into the diverted gas stream at one or more predetermined rates to produce a LDHI-containing gas stream;
  introducing the LDHI-containing gas stream into a coolable portion of the gas conduit, which coolable portion is provided with pressure sensors along the coolable portion;
  cooling the LDHI-containing gas stream passing through the coolable portion of the gas conduit to a predetermined temperature; and
  monitoring pressure of the LDHI-containing gas stream passing through the coolable portion of the gas conduit for a predetermined time range being at least as long as the gas residence time within the gas pipeline;
  whereby a substantially uniform pressure drop along the coolable portion of the gas conduit during the prede- (Continued)

termined time range indicates a LDHI feed rate sufficient to suppress hydrate formation at the predetermined temperature.

28 Claims, 9 Drawing Sheets

(58) Field of Classification Search
USPC .................................. 62/613, 630; 166/279
See application file for complete search history.

(56) References Cited

U.S. PATENT DOCUMENTS

| | | | | |
|---|---|---|---|---|
| 7,025,131 | B2* | 4/2006 | Baugh | E21B 34/066 |
| | | | | 166/248 |
| 8,430,161 | B2* | 4/2013 | Eddy | C09K 8/532 |
| | | | | 166/250.05 |
| 2009/0031755 | A1* | 2/2009 | Amsyari | F25J 1/0022 |
| | | | | 62/613 |
| 2011/0048546 | A1* | 3/2011 | Bjorge | E21B 43/01 |
| | | | | 137/154 |
| 2014/0346033 | A1* | 11/2014 | Kaasa | C10L 3/003 |
| | | | | 203/12 |

* cited by examiner

EXAMINATION PROCESS FOR THE IN SITU DETERMINATION OF RATE OF FEEDING AN INHIBITOR INTO A GAS PIPELINE FOR PREVENTING HYDRATE FORMATION

CROSS REFERENCE TO PRIOR APPLICATIONS

This application is a continuation-in-part of U.S. Ser. No. 14/919,060 filed on Oct. 21, 2015 and claims priority of Hungarian Patent Application No. P1500554 filed on Nov. 24, 2015, each of which is incorporated herein by reference.

FIELD OF THE INVENTION

The invention relates to an examination process for the in situ determination of rate of feeding an inhibitor into a gas pipeline for preventing hydrate formation.

BACKGROUND OF THE INVENTION

When transporting natural gas in a pipeline hydrates may form in the gas as the temperature of the gas decreases. During hydrate formation crystals are formed which can grow and agglomerate thereby forming hydrate plugs in the gas pipeline which hinder the gas transport thereafter. This problem is generally overcome on the one hand by heating the pipeline and on the other hand by feeding anti-hydrate compounds, typically thermodynamic inhibitors such as methanol, glycol or so called LDHI (Low Dosage Hydrate Inhibitor) type of inhibitors, into the pipeline that inhibit hydrate formation. The disadvantage of heating the pipeline is that it increases the cost of the transport of natural gas substantially. The use of methanol and other type of thermodynamic inhibitors is declining as these are strongly contaminating the environment, and require a substantially higher concentration than the LDHI type of inhibitors. Two types of LDHIs are known: the kinetic inhibitors, which decrease the speed of hydrate formation, and the anti-agglomerate inhibitors, which prevent agglomeration of the hydrate particles. In at least 95% of the cases the companies still employ the conventional, environmentally unfriendly methanol or glycol and expensive heating in order to protect gas pipes from hydrate plugs. Application of the environmentally friendly inhibitors is not yet wide-spread due to the higher expenses, although strong ecological interest is tied to it. The novelty of the present complex invention, in its details and as a whole, ensures the cost efficient and safe employment of inhibitors.

Hereinafter the LDHI type of inhibitors will be discussed, which will simply be referred to as LDHI or inhibitor for the sake of simplicity.

Inhibitors of different type and composition are available of which the selection of the most suitable inhibitor and its feeding rate depends on the various parameters of the gas well, the gas pipeline and the gas to be transported. Such parameters are for example the depth of the gas well, its yield, the natural gas condensate content, the stratum water content, and the carbon-dioxide content of the natural gas, the length and material quality of the pipeline, the flow parameters, the expected temperature conditions within the pipeline, etc. The suitable inhibitor is generally chosen by taking a sample from the gas well-head, transporting the sample to a remote laboratory where different inhibitors are added to the sample and measurements are performed in order to determine the efficiency of the inhibitor. The disadvantage of this method is that the composition of the gas sample and the ratio of the gas phase and liquid phase may change during transportation due to chemical reactions taking place inside the sample. A further disadvantage is that the amount of the sample does not allow for investigating hydrate formation at an industrial scale which may substantially influence the usability of the measurement results.

A great disadvantage of the currently employed inhibitor feeding systems is that regular on-site inspection is required for the continuous control of the reliability of operation. Furthermore, the feeding quantity can only be set on-site as well. In case of possible breakdown of operation or of a change of the environmental conditions (for example temperature) this system can only respond with big delay.

Presently, there is no known, complex, inhibitor feeding system and process using on-site measurements with the help of which the feeding of the rather expensive inhibitor into a gas pipeline could be optimized efficiently. The present solutions do not allow for determining the minimal quantity of inhibitor to be fed in, nor does it allow for early detection of a possible malfunction or breakdown of the feeding system.

It is an objective of the present invention to provide a process which overcomes the problems associated with the prior art. In particular, it is an objective of the invention to provide a process, which allows for the in situ determination of the rate of feeding an inhibitor into a gas pipeline for preventing hydrate formation, as well as remote control of the process of inhibitor feeding, thereby contributing to the spreading of the hydrate prevention technology that is based on the use of inhibitors.

SUMMARY OF THE INVENTION

The present invention comprises an examination process for replicating hydrate forming conditions in a gas pipeline and monitoring the effect of a low dosage hydrate inhibitor (LDHI) in suppressing hydrate formation at temperatures encountered in gas pipelines for dynamically determining LDHI feed rate for inhibition of hydrate formation. The process comprises the steps of:

diverting from a gas well a sample gas stream at a preselected rate;

introducing the diverted gas stream into a gas conduit through an inlet of the gas conduit;

feeding LDHI into the diverted gas stream at one or more predetermined rates to produce a LDHI-containing gas stream;

introducing the LDHI-containing gas stream into a coolable portion of the gas conduit, which coolable portion is provided with pressure sensors along the coolable portion;

cooling the LDHI-containing gas stream passing through the coolable portion of the gas conduit to a predetermined temperature; and monitoring pressure of the LDHI-containing gas stream passing through the coolable portion of the gas conduit for a predetermined time period;

whereby a substantially uniform pressure drop along the coolable portion of the gas conduit during the predetermined time period (observation time) indicates a LDHI feed rate sufficient to suppress hydrate formation at the predetermined temperature.

Preferably the preferred predetermined temperature to which the coolable portion is cooled is a temperature below hydrate formation temperature at gas pressures existing in a gas pipeline. The predetermined temperature is preferably between about 0° C. to about 16° C.

Gas observation time within the examined gas pipeline usually is in the range of about 1000 seconds to about 10000 seconds. Preferably, the predetermined observation time is at least twice the gas Residence Time within the coolable portion of the gas conduit. As used herein and in the appended claims, the term "Residence Time" means the time a particular gas molecule is within the coolable portion of the gas conduit and is calculated by a formula Residence Time equals volume of coolable portion of gas conduit divided by volumetric flow rate through the coolable portion of the gas conduit.

Preferably the process further includes the steps of providing an LDHI feeder comprising a telemetric data transmission system for the remote control and monitoring of the LDHI feeder; connecting the LDHI feeder to a feeding point of the gas pipeline; determining a temperature of the examined gas pipeline; and feeding the LDHI into the gas pipeline through the feeding point by the LDHI feeder at a LDHI feed rate sufficient to suppress hydrate formation at a temperature not exceeding the gas pipeline temperature. The gas pipeline temperature may be determined for example along the gas pipeline in the vicinity of the feeding point.

Certain advantageous embodiments of the invention are defined in the attached dependent claims.

DETAILED DESCRIPTION OF THE INVENTION

Figure 1:
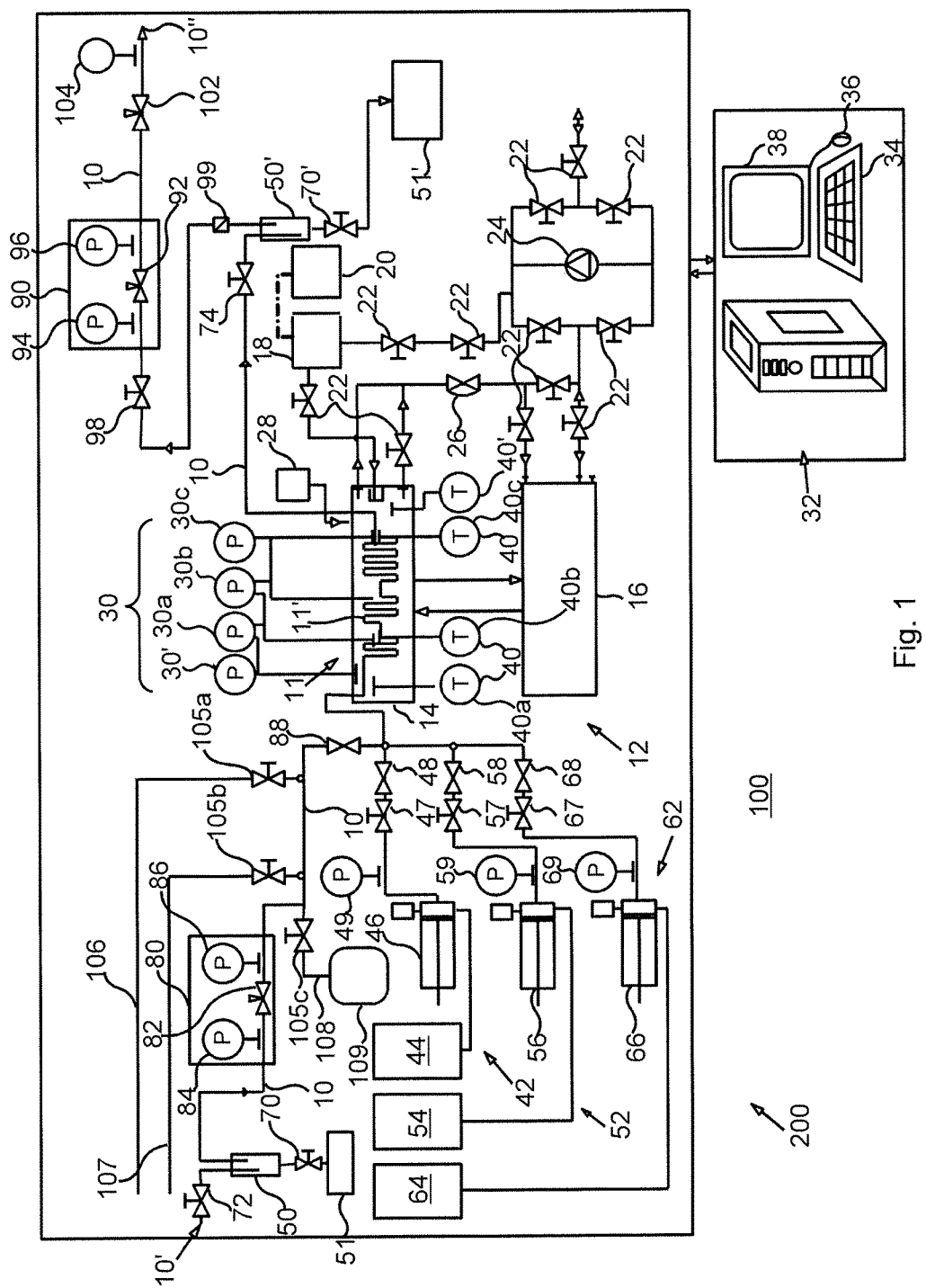
FIG. 1 is a schematic diagram of a preferred embodiment of an industrial scale measuring system for preforming the process according to the invention.

A preferred embodiment of an industrial scale measuring system 200 of an examination system 100 for performing the process according to the invention can be seen in FIG. 1. The examination system 100 may advantageously comprise a laboratory scale measuring system 300 as well (see FIG. 3). The main difference between the industrial scale measuring system 200 and the laboratory scale measuring system 300 is that the gas conduit 10 of the industrial scale measuring system 200 can be connected directly to the well-head of the gas well supplying the gas (natural gas) that is to be examined, whereby the examination may be performed in situ, i.e. on-site at the gas well. Furthermore, the dimensions of the industrial scale measuring system 200 are sufficiently close to the dimensions of the gas pipeline that is used to transport the gas from the gas well, in order to ensure that hydrodynamic and thermodynamic differences do not substantially influence the hydrate formation in the presence of the examined inhibitor.

In contradistinction, the purpose of the optional laboratory scale measuring system 300 is to allow pre-measurements on substantially smaller amounts of gas in order to reduce the number of inhibitors that are to be examined, it is thereby possible to pre-screen in a fast and cost-efficient way which one or more inhibitors should be examined in the industrial scale measuring system 200.

The industrial scale measuring system 200 comprises a gas conduit 10 having a gas inlet 10' which can be connected to a gas well-head. In the context of the invention the term gas well is understood to include any apparatus, formation or location serving as a gas source, for example a reservoir such as an underground reserve cave or artificial tank, and the term well-head is understood to refer to the gas outlet of such gas sources. The examination system 100 can be used in connection with any gas pipeline (either field conduit or pipes of a facility) or technology pipe in which hydrate formation may occur. Gas can be extracted from such gas pipelines as well, in this case the point of extraction (typically a conduit branch) is regarded as the gas well-head. The gas pipeline is connected to the gas well-head for transporting the gas to a gas collection station or any other place of designation. The purpose of the invention is to determine the required rate of feeding a suitable hydrate inhibitor into such a gas pipeline. The gas transported through the gas pipeline remains inside the gas pipeline (between the input and output locations) for a given residence time, thus the inhibitor and its feed-rate is generally considered adequate if it prevents hydrate formation during this residence time, preferably during twice the residence time.

The gas inlet 10' of the gas conduit 10 is connectable to the well-head, preferably to the gate valve of the blind flange of the well-head assembly (Christmas-tree) or to an upper sample outlet of a conduit branch mounted on the gate valve in order to obtain dry gas free of liquid phase from the highest point of the gate valve. The gas inlet 10' of the gas conduit 10 can be connected to the well-head either directly or indirectly (for example through an accessory part that is not part of the examination system 100). In the context of the present invention the gas inlet 10' of the gas conduit 10 is regarded as being connectable to the gas well-head even if it is connectable indirectly, however, after connection continuous gas flow can be ensured from the gas well into the gas conduit 10.

The gas conduit 10 is preferably formed as a pulse line.

The industrial scale measuring system 200 comprises a heat exchanger 12 and the gas conduit 10 comprises a coolable portion 11 which is arranged in the heat exchanger 12. If necessary, the coolable portion 11 may also be heatable as well, thus the term coolable should not be interpreted in a limiting sense.

In the context of the present invention the terms "industrial scale" and "laboratory scale" relating to the measurement systems 200 and 300, respectively, are used for distinguishing purposes only, and do not imply more restriction than if the measuring systems were called "first" and "second" measuring systems 200, 300, respectively. However, it can be said that the dimensions (length, inner diameter) of the coolable portion 11 of the industrial scale measuring system 200 are greater than the dimensions of the corresponding coolable portion 111 (see FIG. 3) of the laboratory scale measuring system 300, preferably its length is at least two times greater, more preferably 5 to 15 times greater. The length of the coolable portion 11 of the industrial scale measuring system 200, which serves for performing the measurements is preferably at least 100 m, and its inner diameter is at least 7 mm in order to be a sufficiently close approximation of the dimensions of the gas pipeline for rendering the modelling reliable. The dimensions of the coolable portion 111 of the laboratory scale measuring system 300 are smaller than this.

The coolable portion 11 of the industrial scale measuring system 200 is preferably formed as a coil pipe 11' the inner diameter of which is chosen so as to avoid capillary effects, in order to ensure better resemblance of the measuring conditions to the hydrodynamic conditions inside the gas pipeline that is connected to the gas well-head. In order to avoid capillary effects the inner diameter is at least 7 mm, more preferably at least 10 mm. In order to reduce the necessary amount of natural gas for the measurement the inner diameter of the coil pipe 11' is preferably not greater than 20 mm. The length of the coil pipe 11' is preferably at least 100 m in order to ensure sufficient heat exchange surface for cooling purposes, and is preferably not more than 200 m, however, longer coil pipes 11' may be used for the simulation of particularly long gas pipelines.

The material properties of the gas conduit 10 and in particular its coolable portion 11 are chosen in accordance with the material properties of the gas pipeline of the gas well in order to render the hydrodynamic and thermodynamic conditions more similar in this regard as well. Since the material of the gas pipelines used at gas wells is generally carbon steel, accordingly, preferably the gas conduit 10, in particular the coil pipe 11' that is arranged within a heat exchange space 14 of the heat exchanger 12, is also made of carbon steel since it is preferred to have the same material properties as that of the gas pipeline in order to ensure that the same hydrodynamic conditions arise along the pipe wall. In case the material of the gas pipeline is acid-proof steel, this is preferably modeled by a coil pipe 11' made of acid-proof steel.

The heat exchanger 12 preferably comprises a heat exchange space 14 wherein the coil pipe 11' of the coolable portion 11 is arranged and which can be filled with a cooling medium. The heat exchanger 12 further comprises a tank 16 for discharging the cooling medium, a heat exchange unit 18 for cooling the cooling medium to a desired temperature and a deep freezer aggregator unit 20. The aforesaid components of the heat exchanger 12 may be connected to each other for example according to the basic circuit diagram illustrated in FIG. 1, through ball valves 22, and a pump 24 circulates the cooling liquid and helps to charge or discharge the heat exchange space 14 and the tank 16 of the heat exchanger 12. Preferably, the liquid level within the tank 16 can be monitored for example by liquid level sensors and/or through a sight glass 26 shown in FIG. 1.

The industrial scale measuring system 200 preferably comprises an air heater 28 in connection with the heat exchange space 14 of the heat exchanger 12 for reheating the gas transported in the coil pipe 11' in case of hydrate plug formation therein as will be explained in more detail later on.

Pressure measuring devices 30 are arranged at minimum two locations but preferably at four locations along the coolable portion 11 in order to determine the pressure difference between the consecutive locations. According to the present embodiment the pressure measuring devices 30 comprise a first pressure gauge 30' and three differential pressure gauges 30a, 30b, 30c arranged downstream thereof, and the pressure is measured at the inlet of the coil pipe 11', at ¼ of its length, at half of its length and at its outlet as illustrated in FIG. 1, whereby pressure difference can be measured at three different positions. In case of hydrate formation the location where the hydrate formation occurs can be deducted from the ensuing pressure difference.

The pressure gauge 30' and the differential pressure gauges 30a, 30b, 30c are preferably in connection with a measurement controlling computer 32 such as to be able to transmit the measurement data to the computer 32, which evaluates the received data with the help of a measurement controlling program. A data transmission connection between the pressure measuring devices 30 and the computer 32 can be ensured through wired or wireless connection (e.g. WiFi connection) as is known per se. In the context of the present invention the term computer is used in a broad sense including any hardware device that is suitable for collecting and processing data and, based thereon, controlling units of the examination system 300, for example desk top computer, laptop, tablet, smart phone, microcontroller, etc. The computer 32 preferably comprises one or more input devices (for example keyboard 34, mouse 36, etc.), one or more output devices (for example display 38, printer, etc.) and may comprise interfaces that can serve as both input and output devices (for example touch screen, CD/DVD reader/writer, etc.).

Preferably, thermometers 40a, 40b and 40c are connected to the coolable portion 11 of the gas conduit 10 of the industrial scale measuring system 200 for measuring the temperature of the gas transported within the coil pipe 11' at minimum two locations but preferably at three locations and a forth thermometer 40' is provided for measuring the temperature of the cooling liquid. The thermometers 40a, 40b, 40c and 40' preferably transmit the measurement data to the computer 32.

The industrial scale measuring system 200 preferably further comprises an inhibitor feeding system 42 which is connected to the gas conduit 10 between the gas inlet 10' and the coolable portion 11. The inhibitor feeding system 42 comprises an inhibitor tank 44 and a feeding pump 46, preferably an electric feeding pump connected therewith, which may be connected to the gas conduit 10 for example through ball valve 47 and check valve 48 as illustrated in FIG. 1. Preferably a pressure gauge 49 is provided between the feeding pump 46 and the ball valve 47.

The gas (natural gas) transported through the gas pipeline from the gas well comprises liquid phase stratum water and/or natural gas condensate in the amount characteristic of the gas well, the presence of which may influence the hydrate formation and the formation of hydrate plugs. The inventor has recognized that the amount of the stratum water and natural gas condensate that can be measured in the gas pipeline does not necessarily correspond to the proportions present in the gas conduit 10 of the industrial scale measuring system 200, for which reason it is preferred to separate the liquid phase (and any solid contaminants) from the examined gas by a separator 50, and feed stratum water and natural gas condensate in the proportions measurable in the transport pipeline into the gas conduit 10 upstream of the coolable portion 11. The industrial scale measuring system 200 preferably comprises for this purpose a stratum water feeding system 52 and a natural gas condensate feeding system 62 both of which are connected to the gas conduit 10 between the separator 50 and the coolable portion 11.

The stratum water feeding system 52 comprises a stratum water tank 54 and a feeding pump 56, preferably a pneumatic feeding pump, connected therewith, which may be connected to the gas conduit 10 for example through a ball valve 57 and check valve 58 as illustrated in FIG. 1. Preferably a pressure gauge 59 is provided between the feeding pump 56 and the ball valve 57.

Similarly, the natural gas condensate feeding system 62 comprises a natural gas condensate tank 64 and a feeding pump 66, preferably a pneumatic feeding pump, connected therewith, which may be connected to the gas conduit 10 for example through a ball valve 67 and check valve 68 as illustrated in FIG. 1. Preferably a pressure gauge 69 is provided between the feeding pump 66 and the ball valve 67.

The three feeding systems 42, 52, 62 can be formed as a single integrated system.

The separator 50 can be any kind of known device suitable for separating liquid. Preferably, a tank 51 is connected to the separator 50 through a ball valve 70 for collecting the separated liquid and solid contaminants. The gas inlet 10' is preferably separated from the separator 50 by a ball valve 72.

Similarly, a separator 50' can be applied downstream of the coolable portion 11 of the gas conduit 10 in order to separate the natural gas condensate, stratum water and inhibitor that has been fed into the gas stream. Preferably, a tank 51' is also connected to the separator 50' through a ball valve 70'. Preferably, the separator 50' is connected to the portion of the gas conduit 10 exiting the heat exchanger 12 through a ball valve 74.

If the gas inlet 10' of the gas conduit 10 is connected to the gas well, a pressure regulator 80 is preferably connected to the gas conduit 10 downstream of the separator 50 following the gas inlet 10' because the pressure at the gas well is generally somewhat higher than within the gas pipeline and the pressure regulator 80 serves to reduce the pressure of the transported gas in order to reproduce the pressure conditions within the gas transport pipeline connected to the gas well. It is also possible to connect the gas inlet 10' of the gas conduit 10 to a notch on the gas pipeline in which case the pressure regulator 80 is not required.

According to a preferred embodiment the pressure regulator 80 comprises a pressure reducing valve 82 and pressure gauges 84 and 86 connected upstream and downstream thereof, in order to visually present the entry and exit pressure values. The measurement data of the pressure gauges 84 and 86 can be transmitted to the computer 32, which may control the pressure reducing valve 82. The pressure regulator 80 is preferably connected to the coil pipe 11' of the coolable portion 11 through a check valve 88.

A further pressure regulator 90 may be provided upstream of the gas outlet 10" of the gas conduit 10 for setting the pressure of the gas exiting the gas conduit 10. According to a preferred embodiment the pressure regulator 90 comprises a pressure reducing valve 92 and pressure gauges 94 and 96 connected upstream and downstream thereof, in order to visually present the entry and exit pressure values. The pressure regulator 90 is preferably connected to the separator 50' through a check valve 98.

The pressure regulator 90 is preferably followed by a choke valve 102 for setting the flow rate of the gas inside the gas conduit 10 which can be measured by a flowmeter 104. The flowmeter 104 may transmit measurement data to the computer 32 over a data transmission connection therewith. The pressure regulator 90, the choke valve 102 and the flowmeter 104 are preferably protected from any solid or liquid contaminants that may eventually pass the separator 50' by a filter 99.

Preferably a conduit 106 for introducing hot water, a conduit 107 for introducing air and/or a conduit 108 for introducing nitrogen is connected to the gas conduit 10 of the industrial scale measuring system 200 between the gas inlet 10' and the coolable portion 11 through ball valves 105a, 105b, 105c respectively. The hot water conduit 106 is advantageously connected to the local hot water network or it may be connected to the cold water network with the interposition of a water heater. The nitrogen is preferably introduced into the conduit 108 from a nitrogen tank 109.

The examination system 100 comprising the industrial scale measuring system 200 and optionally the laboratory scale measuring system 300 is preferably formed as a mobile station, whereby it can be transported to the location of the gas well, which is to be examined, and the measurements can be performed there. The examination system 100 is preferably provided in a container, thus the measuring apparatuses and accessories located in the container can be easily installed on the site of the examined well, whereby the measurements for preventing hydrate formation can be performed substantially faster and more efficiently, furthermore, the problems associated with the transport of the gas sample can be eliminated. Further advantage of the local (in situ) measurements is that the different stratum water and natural gas condensate content of the well flow can be easily taken into account by feeding the stratum water and natural gas condensate obtained from the well into the examination system 100. Since the efficiency of the examinations depend considerably on the number of measurements, hence the in situ performance of a high number of measurements can substantially reduce the time required to analyze a gas well; whereas the conventional measurements performed in laboratories inside remote buildings required months, the same measurements may be performed within a week with the help of the mobile station.

The inner space of the container is preferably monitored with a gas detector (not shown) in order to eliminate the risk of a gas explosion, which detector signals at 10% of LEL (Lower Explosive Limit), turns a ventilation fan on at 20% of LEL, and shuts off the electric system at 30% of LEL.

The energy source of the mobile examination system 100 is preferably a current generator.

The industrial scale measuring system 200 is applied as follows.

According to a first step of the process according to the invention the quantity of the inhibitor that is to be fed into the gas pipeline is determined with the help of the industrial scale measuring system 200. Before starting the measurements the tank 16 of the heat exchanger 12 is filled with a cooling liquid, for example a 3:1 ratio mixture of glycol to distilled water, through the ball valve 22.

At the start of the measurement the heat exchange space 14 is filled with the cooling liquid from the tank 16 with the help of the pump 24. The cooling liquid is continuously circulated in the heat exchange space 14 by the deep freezer aggregator unit 20 which is thereby cooled to the desired temperature. The flow can be monitored through the sight glass 26.

The natural gas to be examined is obtained from the well, through the conduit branch of the well head, which is then transported through a pulse line to the gas inlet 10' of the gas conduit 10 of the measuring system 200. The natural gas enters the industrial scale measuring system 200 through the ball valve 72 arranged at the gas inlet 10'. The liquid phase (practically stratum water and natural gas condensate) and solid contaminants are separated from the introduced natural gas with the help of the separator 50.

The required pressure for the measurement is then set by the pressure regulator 80.

In order to examine the formation of hydrates the conditions within the gas pipeline have to be modeled. This is done by determining the amount of stratum water and natural gas condensate carried in the gas pipeline and a corresponding amount of stratum water and natural gas condensate is fed into the gas conduit 10 after the liquid phase has been separated but upstream of the entrance of the coolable portion 11. The amounts to be fed into the gas conduit 10 can be determined based on data of prior measurements (possibly conducted by third parties).

The feeding of the inhibitor, stratum water and natural gas condensate is ensured by the feeding systems 42, 52, 62 such that the inhibitor, stratum water and natural gas condensate are fed into the gas conduit 10 from the tank 44, 54, 64 of each feeding system 42, 52, 62 by the electric or pneumatic feeding pumps 46, 56, 66, respectively. The feed rate of the inhibitor is set in accordance with the examination (such an examination may be for example whether or not a given mass flow of a given inhibitor is sufficient to prevent hydrate formation at a given temperature). The stratum water and the natural gas condensate are fed into the natural gas at the amount necessary to obtain a composition ratio corresponding to the composition ratio within the natural gas transported inside the gas pipeline.

The gas containing the added inhibitor, stratum water and natural gas condensate is transported to the coolable portion 11 of the gas conduit 10, which is arranged inside the heat exchange space 14 of the heat exchanger 12, where the gas is cooled to a predetermined temperature with the cooling liquid. In the context of the present invention the predetermined temperature to which the gas is cooled is the lowest temperature reached by the gas stream in the coolable portion 11. When using the heat exchanger 12 the theoretical minimum for the gas temperature is the temperature of the cooling liquid. In practice the temperature of the cooling liquid can be regarded as the predetermined temperature. The temperature is measured continuously at four locations (at the inlet and outlet of the coil pipe 11, at ¼ of its length, furthermore the temperature of the cooling liquid is measured) by the thermometers 40a, 40b, 40c and 40'.

The drop of pressure of the natural gas within the heat exchange space 14 is measured at three locations by the pressure measuring devices 30 as explained earlier, and it is determined from the measured pressure difference whether or not a hydrate plug was formed along the measured portion, which hydrate plug obstructs the flow and thereby increases the pressure.

The resulting pressure drop values and temperature data are transmitted to the computer 32 controlling the measurement, which then processes the data and preferably displays the data on the display 38. The computer 32 uses the data to determine the result of gas hydrate formation in connection with the gas obtained from the given gas well. The computer 32 preferably also monitors the measurement data of the pressure gauges 49, 59, 69 belonging to the feeding pumps 46, 56, 66, and may control the controllable elements thereof based on the measurement data.

The analysis performed by the examination system 100 helps in operating an inhibitor feeder 290 installed permanently at the given well with the best efficiency. The most efficient industrial inhibitor can be selected and the quantity of the inhibitor applied at the well can be reduced.

After examination, the natural gas is freed from the added stratum water, natural gas condensate and eventually any solid contaminants by the separator 50' and the filter 99, and after having passed the flowmeter 104 it is conducted out from the container. The desired flow rate is set by the choke valve 102 having regard to the feed-back of the flowmeter 104.

After the system freezes, i.e. after a hydrate plug is formed, the coil pipe 11' arranged within the heat exchanger 12 has to be heated in order to eliminate the hydrate plug. The heating is performed by discharging the cooling medium from the heat exchange space 14 of the heat exchanger 12 into the tank 16, after which the coil pipe 11' is heated by the air heater 28 by blowing in air of approx. 40-50° C. until the plug is dissolved. The cooling medium is pumped back into the heat exchange space 14 from the tank 16, whereby substantially less time and energy is required for obtaining the necessary cooling temperature as compared to the case where the cooling medium is heated in the heat exchange space 14 for eliminating the hydrate plug.

The examination of the hydrate formation is performed by the industrial scale measuring system 200 for more than one type of inhibitors and/or more than one feed rate and/or by cooling the gas to more than one temperature. After each measurement the cooling medium is discharged into the tank 16, then the system is washed with hot water coming through the conduit 106, finally nitrogen is blown through the system, which is introduced from the tank 109 through the conduit 108. It is also possible to mix an inhibitor-neutral cleaning agent to the hot water.

The industrial scale measuring system 200 according to FIG. 1 has been built and the results of measurements performed therewith can be seen in FIGS. 2a-2c and will be discussed hereinafter.

EXAMPLES

Example 1

The length of the coil pipe 11' of the built measuring system 200 was 160 m, its inner diameter was 10 mm. The volume flow rate of the natural gas was set to 150 l/min with the help of the pressure regulator 90, which value was measured at normal atmospheric pressure. The gas was freed from stratum water, natural gas condensate and solid contaminants and into this gas stream stratum water was fed at a rate of 14 ml/min, and natural gas condensate was fed at a rate of 14 ml/min by the stratum water feeding system 52 and the natural gas condensate feeding system 62, respectively. An inhibitor formed as the 1:1 ratio mixture of anti-agglomerate type GH-86 LDHI concentrate (sold by MOL-LUB Ltd., Almásfüzitö, Hungary) and natural gas condensate was fed into the gas conduit 10 at a rate of 0.29 ml/min with the help of the feeding system 42.

The temperature of the cooling liquid within the heat exchange space 14 of the heat exchanger 12 was 2° C., which was continuously monitored by the thermometer 40'. The measurement is preferably performed for 1.5 times longer than the Residence Time of the natural gas inside the measured gas conduit. In the present case the measurement was only performed for 4000 sec.

Figure 2A:
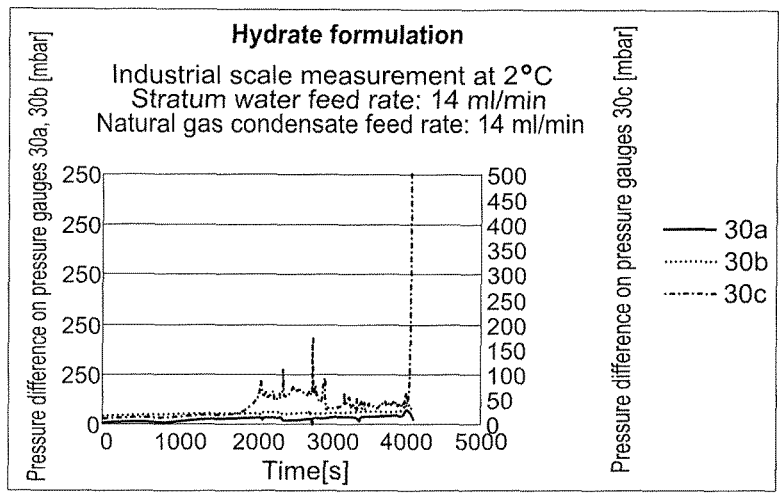
FIG. 2a is a pressure difference diagram obtained in a measurement performed by the measuring system according to FIG. 1.

The pressure differences measured by the differential pressure gauges 30a, 30b and 30c are plotted against time in FIG. 2a. As can be seen the differential pressure gauges 30a and 30b measured about 0 bar value during the whole time, while the pressure difference measured by the differential pressure gauge 30c suddenly increased around 2000 sec, then it fluctuated strongly and finally reached its upper measuring limit at about 4000 sec. From this it can be concluded that at 2° C. after 2000 sec the delivered inhibitor is no longer able to prevent gas hydrate formation, as a consequence gas hydrate starts to form along the inner surface of the coil pipe 11', whereby the penetrable cross-section decreases, which leads to a pressure difference. The pressure difference fluctuation is due to the fact that the gas flow is often able to wash away the hydrate particles from the pipe wall, whereby the pressure difference is eliminated or reduced along the given pipe portion. It can also be concluded from the measurement data provided by the differential pressure gauges 30a, 30b, 30c, that gas hydrate formation occurred beyond the middle point of the coil pipe 11', since the third differential pressure gauge 30c measured substantial pressure difference. The sudden increase of pressure difference at about 4000 sec indicates the formation of a hydrate plug, the coil pipe 11' becomes impenetrable to a great extent, whereby the pressure difference drastically increases between the two sides of the hydrate plug.

Figure 2B:
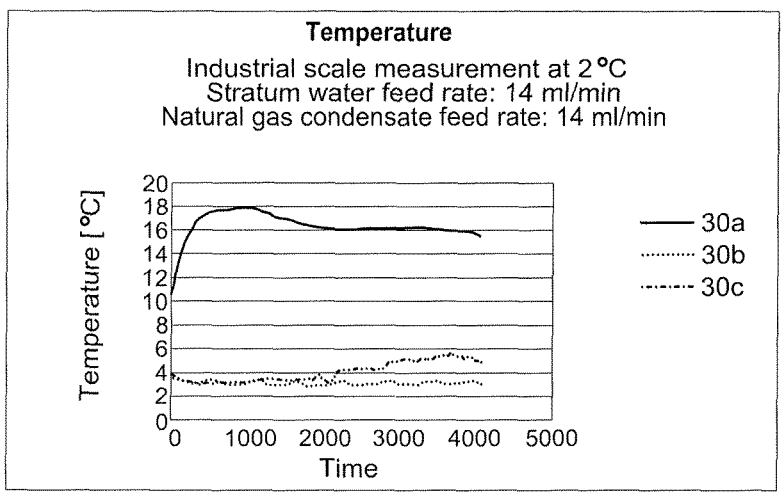
FIG. 2b is a temperature diagram obtained in a measurement performed by the measuring system according to FIG. 1.

The temperatures measured by the thermometers 40a, 40b, 40c are plotted against time in FIG. 2b. The first thermometer 40a measures the temperature at the inlet of the coil pipe 11' where the cooling liquid that is circulated in the heat exchange space 14 has not yet cooled the gas, thus this temperature is substantially higher. The second thermometer 40b is arranged at the third of the coil pipe 11', while the third thermometer 40c is arranged in the vicinity of the outlet. The third thermometer 40c should measure approximately the same but always somewhat lower temperature than the second thermometer 40b, however, as can be seen, after about 2000 sec the temperature measured by the third thermometer 40c started to increase and surpassed the temperature measured by the second thermometer 40b, although the temperature along the coil pipe 11' should be closer and closer to the 2° C. temperature of the cooling liquid. The deviation is due to the fact that the hydrate formation is an exoterm process, meaning that it is accompanied by heat production, whereby the temperature increases along the pipe portion where gas hydrate starts to form. This phenomenon allows for deducting gas hydrate formation from the temperature measurement.

Figure 2C:
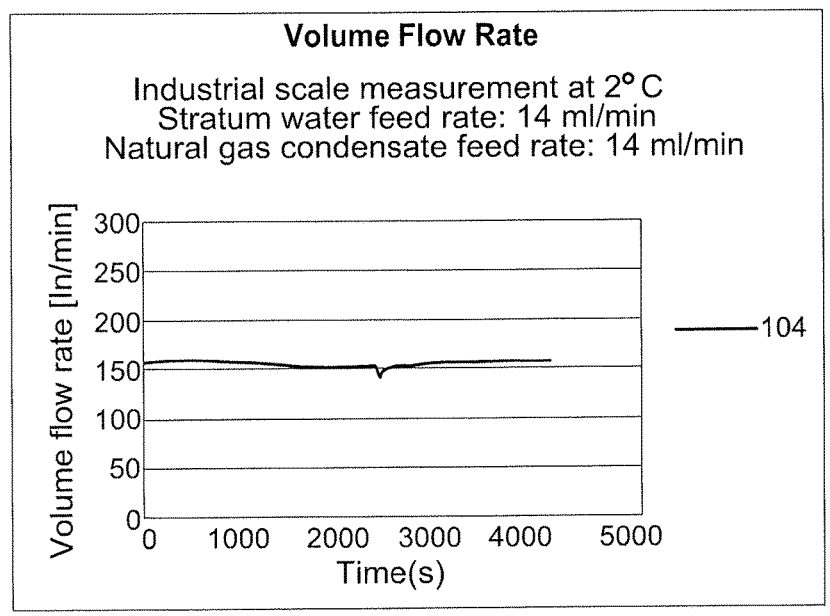
FIG. 2c is a volume flow rate diagram obtained in a measurement performed by the measuring system according to FIG. 1.

FIG. 2c shows the volume flow rate measured by the flowmeter 104 at normal atmospheric pressure and is plotted against time. The measurement data delivered by the flowmeter 104 also allows for determining whether or not hydrate formation occurred because, due to the hydrate deposition, the volume flow rate of the gas temporarily decreases, then it is compensated as can be seen in FIG. 2c. Naturally, in case the system freezes, i.e. when such hydrate plug is formed which seals off the coil pipe 11' completely, then the volume flow rate drops to zero.

The process allows for examining whether or not gas hydrate is formed inside the coolable portion 11 of the gas conduit 10 when changing the type and feed rate of the inhibitor and the temperature of the cooling liquid. The measurement is performed for at least as long as the natural gas would dwell (travel) inside the gas pipeline, whereby it is possible to experimentally model whether or not gas hydrate would form inside the gas pipeline at the given temperature and in the presence of the given inhibitor. Since the objective of the invention is to reliably prevent gas hydrate formation, thus it is expedient to measure for a longer period than the residence time of the gas when transported along the gas pipeline. It has been found that it is advantageous to measure for a time period of at least 1.5 times the residence time of the natural gas transported within the gas pipeline, in this way the inhibitor quantity (concentration) that is deemed sufficient in the course of the measurement has been found adequate in practice to prevent hydrate plug formation along the whole length of the gas pipeline, while it does not result in feeding an excessive amount of inhibitor into the gas pipeline.

The examination system 100 preferably also comprises a laboratory scale measuring system 300 (see FIG. 3) in addition to the industrial scale measuring system 200, which allows for faster and less expensive pre-measurements performed with a smaller quantity of gas in order to pre-screen the possible inhibitors.

The components of the laboratory scale measuring system 300 are similar to that of the industrial scale measuring system 200, for which reason the following description of the laboratory scale measuring system 300 concentrates mainly on the differences.

A gas inlet 110' of a gas conduit 110 of the laboratory scale measuring system 300 transporting the examined gas (natural gas) is preferably connected to the gas well-head, or to a conduit branch attached thereto, or to a gas bottle 113 containing a gas sample from which stratum water and natural gas condensate have been separated. The gas bottle 113 can be preferably a commercially available bottle of standard size and pressure range.

The pressure of the gas introduced into the gas conduit 110 can be set to the value required for the examination by a pressure regulator 180. The pressure regulator 180 preferably comprises a pressure reducing valve 182 and pressure gauges 184 and 186 connected upstream and downstream thereof, which can be connected to the same computer 32 as the measuring devices of the industrial scale measuring system 200. It should be appreciated that preferably all measuring devices of the laboratory scale measuring system 300 may be connected to the same computer 32 or to another computer of similar function through wired or wireless connection allowing for data transmission.

The pressure regulator 180 is preferably connected to a coolable portion 111 of the gas conduit 110, that is formed as a measuring cell 111' and is arranged within a heat exchange space 114 of a heat exchanger 112, through a two-way valve 172. A container 116 is connected to the heat exchange space 114 for discharging the cooling agent therein.

A liquid cooler 118 is connected to the heat exchange space 114 of the heat exchanger 112 for cooling the cooling liquid with any known technology.

The cooling liquid that has been cooled to the desired temperature is preferably introduced into the heat exchange space 114 of the heat exchanger 112 from the liquid cooler 118.

The measuring cell 111' is also a pipe, the dimensions of which are chosen such as to allow for fast and cost efficient measurements, i.e. the gas and inhibitor are used in small amounts. Accordingly, the inner diameter of the measuring cell 111' is between 3 mm and 5 mm, preferably approx. 4 mm; its outer diameter is approx. 6 mm; its length is preferably not more than 50 m, more preferably not more than 30 m, for example approx. 20 m. The measuring cell 111' may optionally have a two-part structure: for example it can be made up of a 6 m long portion and a 12 m long portion, and a pressure gauge and thermometer can be arranged between the two portions.

The gas conduit 110, in particular the measuring cell 111' arranged in the heat exchange space 114 of the heat exchanger 112 is preferably made of carbon-steel, or acid-proof steel in case the gas pipeline is made of acid-proof steel as explained in connection with the industrial scale measuring system 200.

Pressure measuring devices 130 are arranged at minimum two locations but preferably at three locations along the coolable portion 111 in order to determine the pressure difference between the consecutive locations. According to the present embodiment the pressure measuring devices 130 are differential pressure gauges 130a and 13b and the pressure is measured at the inlet of the coil pipe 111', at ⅓ of its length, and at its outlet, whereby pressure difference can be measured at two different positions. In case of hydrate formation the location where the hydrate formation occurs can be deducted from the ensuing pressure difference.

Preferably, thermometers 140 are connected to the coolable portion 111 of the gas conduit 110 for measuring the temperature of the gas transported within the measuring cell 111' at minimum two locations but preferably at three locations by three thermometers 140a, 140b, 140c and a forth thermometer 140' is provided for measuring the temperature of the cooling liquid. The thermometers 140a, 140b, 140c, 140' preferably transmit the measurement data to the computer 32.

Figure 3:
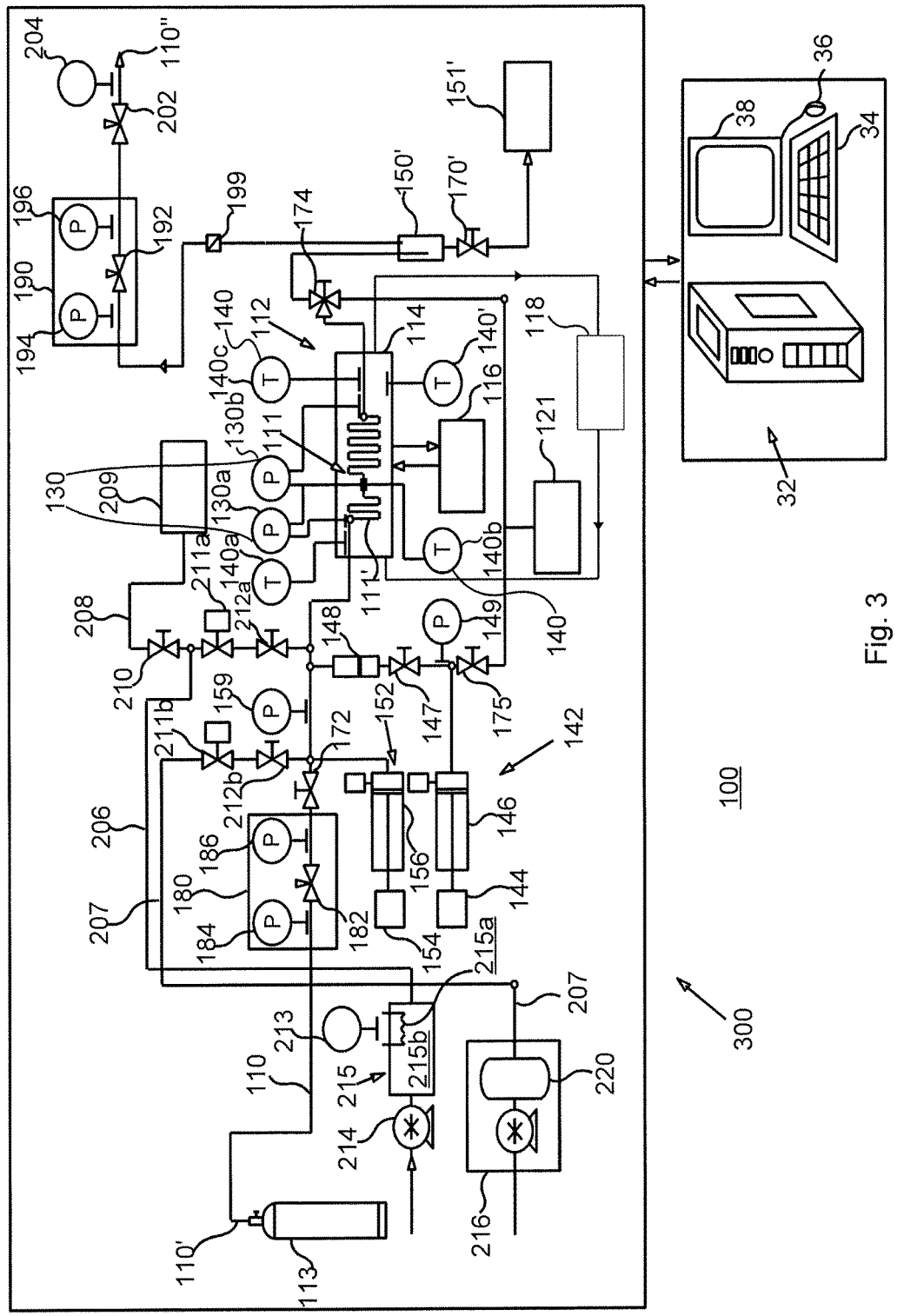
FIG. 3 is a schematic diagram of a preferred embodiment of a laboratory scale measuring system for performing the process according to the invention.

The laboratory scale measuring system 300 preferably further comprises an inhibitor feeding system 142, which is connected to the gas conduit 110 upstream of the coolable portion 111. The inhibitor feeding system 142 comprises an inhibitor tank 144 and a feeding pump 146, preferably an electric feeding pump connected therewith, which may be connected to the gas conduit 110 for example through a two-way valve 147 and a floating piston cell 148 as illustrated in FIG. 3. The floating piston cell 148 serves to inject the hydrate inhibitor into the gas. Preferably a pressure gauge 149 is provided between the feeding pump 146 and the ball valve 147.

The liquid phase and any solid contaminants have been preferably separated in advance from the gas sample used in the laboratory scale measuring system 300, or these are separated in a separator installed at the gas well. Stratum water and natural gas condensate are fed into the gas conduit 110 upstream of the coolable portion 111 in the amount characteristic for the gas well. The natural gas condensate is preferably mixed with the inhibitor, and injected into the gas conduit 110 by the inhibitor feeding system 142, while a separate stratum water feeding system 152 is used for adding the stratum water. It is also conceivable to provide a separate feeding system for the natural gas condensate. The stratum water feeding system 152 comprises a stratum water tank 154 and a feeding pump 156, preferably an electric feeding pump. Preferably a pressure gauge 159 is provided between the feeding pump 156 and the inlet of the inhibitor feeding system 142.

The measurement data of the pressure gauges 149, 159 are preferably also transmitted to the computer 32, which may optionally control the feeding systems 142, 152 using this data.

Preferably, a separator 150' is applied downstream of the coolable portion 111 of the gas conduit 110 for the deposition of the liquids condensed from the gas flow, primarily for the separation of the natural gas condensate, stratum water and inhibitor that has been fed into the gas stream. Preferably, a tank 151' is also connected to the separator 150' through a two-way valve 170'. Preferably, the separator 150' is connected to the portion of the gas conduit 110 exiting the heat exchanger 112 through a three-way valve 174. The three-way valve 174 allows for discharging into the tank 121 a washing liquid that is passed through the gas conduit 110 when it is being washed. The tank 121 is preferably connected to the inhibitor feeding system 142 through a valve 175 as can be seen in FIG. 3.

A pressure regulator 190 is preferably provided upstream of the gas outlet 110" of the gas conduit 110 for setting the pressure of the gas exiting the gas conduit 110. According to a preferred embodiment the pressure regulator 190 comprises a pressure reducing valve 192 and pressure gauges 194 and 196 connected upstream and downstream thereof, in order to visually present the entry and exit pressure values. The measurement data of the pressure gauges 194, 196 may be transmitted to the computer 32. The pressure regulator 190 is preferably connected to the separator 150' through a filter 199.

The pressure regulator 190 is preferably followed by a choke valve 202 and a flowmeter (mass flow meter) 204 for setting the flow rate of the gas inside the gas conduit 110. The flowmeter 204, just like the other measuring devices, may transmit measurement data to the computer 32 over a data transmission connection therewith. The flowmeter 204 is preferably protected from any solid or liquid contaminants that may eventually pass the separator 150' by a filter 199.

Preferably a conduit 206 for introducing hot water, a conduit 207 for introducing air and a conduit 208 for introducing chemical agents is connected to the gas conduit 110 of the laboratory scale measuring system 300 upstream of the coolable portion 111 through subsequent magnetic valves 211a, 211b and two-way valves 212a, 212b, respectively, as can be seen in FIG. 3. The magnetic valves 211a, 211b are preferably also controlled by the computer 32, and compressed air and washing water are introduced into the gas conduit 110 through these valves 211a, 211b when the gas conduit 110 is being cleaned.

The hot water conduit 206 is preferably connected to the local cold water network. The cold water is pumped to a water heater 215 connected to the conduit 206 by a pump 214. The water heater 215 heats the cold water by a heating body 215a and stores the hot water in a tank 215b or the hot water is provided as it runs through the heating body 215a without being stored. The water temperature can be set by a temperature regulator 213 manually or optionally by the computer 32. Another possibility is to connect the hot water conduit 206 to the hot water network.

Preferably, the chemical agent is introduced into the conduit 208 from a tank 209, and the conduit 208 can be closed off by a separate valve 210.

Preferably a compressor 216 is connected to the air introducing conduit 207 for venting and drying the gas conduit 110 between the measurements. The compressor 216 can be any known device, for example a device providing maximum 6-8 bar pressure. The compressor 216 typically comprises an air tank 220.

The laboratory scale measuring system 300 is applied as follows.

The examined natural gas is introduced into the gas conduit 110. The natural gas passes the pressure regulator 180 before entering the coolable portion 111 of the gas conduit 110 that is arranged in the heat exchanger 112. The valves 212a and 212b are kept closed during the measurement.

The examined gas is introduced into the coolable portion 111 through the valve 172. The hydrate inhibitor needs to be mixed to the examined gas in advance, which can be accomplished by the feeding pump 142 in accordance with the pre-set feeding rate. The inhibitor is stored in the tank 144 together with the required amount of natural gas condensate before starting the measurement.

The stratum water must also be ensured for the measurements, which can be fed from the tank 154 by the feeding system 152.

The heat exchange space 114 of the heat exchanger 112 is cooled to the extent required for the measurement by the cooling liquid provided by the liquid cooler 118. The measuring cell 111' of the coolable portion 111 of the gas conduit 110, made up of two portions, is arranged inside the heat exchange space 114.

The pressure drop is measured between three locations within the measuring cell 111 by the differential pressure gauges 130a and 130b as explained earlier, and the measurement data is collected by the computer 32 for the purpose of determining hydrate formation. The temperature is measured at the inlet and outlet of the measuring cell 111' and between the two portions of the measuring cell 111', furthermore, the temperature of the cooling medium is also measured inside the heat exchange space 114, and the data is transmitted to the computer 32.

Downstream of the coolable portion 111 the gas can be conducted, through the three-way valve 174, to the separator 150' and then to the filter 199 in order to separate the stratum water, natural gas condensate and solid contaminants. The gas flows from the filter 199 to the pressure regulator 190 from where it flows to the choke valve 202 and the flowmeter 204. The choke valve 202 has a high resolution fine regulator with which the desired flow parameters can be set, which are measured by the flowmeter 204.

The examined gas exits the measuring system 300 through the gas outlet 110", and exits the container.

Hydrate formation is also examined by the laboratory scale measuring system 300 in different quantities The examination of the hydrate formation is performed by the laboratory scale measuring system 300 for an inhibitor added in different quantities and/or more than one type of inhibitors and/or at least at two given temperatures. Typically more than one type of commercially available inhibitors are examined in order to measure only those types in the industrial scale measuring system 200 which could be efficient according to the laboratory measurements.

After each measurement the gas conduit 110 is washed with hot water and chemicals, and high pressure air is blown through the system. The water required for the washing phase is obtained from the water heater 215, which is connected to the pump 214 that is connected to the cold water network. The water heated by the heating body 215a and stored in the tank 215b of the water heater 215 is introduced into the gas conduit 110 through the conduit 206. Naturally, the water heater may be a continuous flow water heater, in which case the water only dwells temporarily inside the tank 215b, while it is being heated.

In case of hydrate formation the cooling liquid is preferably discharged from the heat exchange space 114 into the container 116, after which the gas conduit 110 is washed. For this, chemicals are added to the hot water from the tank 209 through the conduit 208 and the valve 210.

The washing liquid enters the measuring cell 111' through the magnetic valve 211a and the valve 212a. During washing the valve 172 must be closed and the three-way valve 174 is set such that the washing liquid flows into the tank 121. The valve 212b must be closed during the washing phase.

The drying phase following the washing phase is preferably performed by the air introduced through conduit 207, the pressure of which is set by the compressor 216. The pressure is preferably about 30 bar. The air can be introduced into the measuring cell 111' through the magnetic valve 211b and the valve 212b. When blowing-off the air the three-way valve 174 is set to its measurement state, in which state the air exits the system through the natural gas outlet and is lead outside of the container.

The construction of the laboratory scale measuring system 300, serving to examine the formation of hydrates and the performance of hydrate inhibiting preparations, is such that it can be easily arranged within a container and it can be transported without risk of failure. The devices and accessory components are also sufficiently secured.

Figure 4:
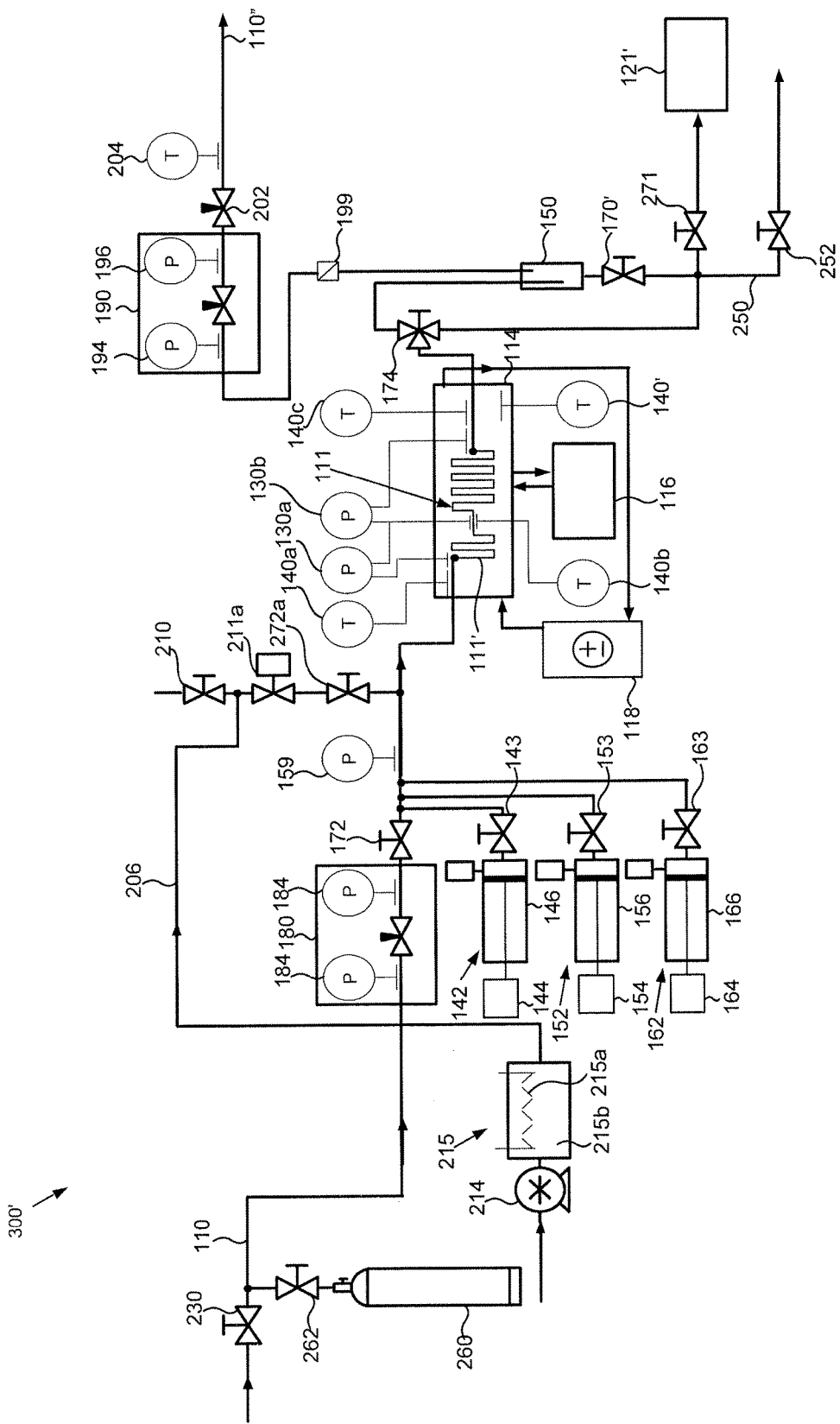
FIG. 4 is a schematic diagram of an alternative laboratory scale measuring system.

FIG. 4 shows another exemplary embodiment of the laboratory scale measuring system 300' according to the invention. For the sake of simplicity only the differences will be discussed in detail with regard to the previously presented laboratory scale measuring system 300. Same components are indicated with the same reference signs.

According to this embodiment the gas that is used for the measurement is extracted from the gas pipeline transporting the natural gas or from the well head as explained in connection with the industrial scale measuring system 200. The extracted gas preferably enters the gas conduit 110 of the laboratory scale measuring system 300' through valve 230.

According to the present embodiment the natural gas condensate is not mixed with the inhibitor, thus a separate inhibitor feeding system 142 is provided for delivering the inhibitor and a separate natural gas condensate feeding system 162 is provided for delivering the natural gas condensate into the gas conduit 110. The inhibitor feeding system 142 comprises, in this case as well, an inhibitor container 144 and a feeding pump 146 connected therewith. Similarly, the natural gas condensate feeding system 162 comprises a natural gas condensate container 164 and a feeding pump 166, preferably an electric feeding pump, connected therewith.

The inhibitor feeding system 142, the stratum water feeding system 152 and the natural gas condensate feeding system 162 are preferable connected to the gas conduit 110 upstream of the pressure gauge 159 through valves 143, 153, 163.

A container 116 is connected to the heat exchange space 114 of the heat exchanger 112 for discharging the cooling agent, as well as a liquid cooler 118 for cooling the cooling liquid by any known technology.

According to the present embodiment it is possible to allow the natural gas to exit through conduit 250 and valve 252 downstream of the separator 150 when it is not required to measure with the flowmeter 204, for example because the measurement has ended.

A further difference is, that according to this embodiment the gas conduit 110 is blown through with nitrogen gas after finishing the measurement instead of washing it with a chemical agent and blowing hot air through it. The nitrogen gas is introduced into the gas conduit 110 from a nitrogen bottle 260 through a valve 262, and it is first discharged through the conduit 250 and then through the gas outlet 110".

The possibility of employing chemical washing may be retained in this case as well. Liquid containing chemicals may be delivered through the valve 210, for example such that it is possible to connect a tank 209 containing the chemical liquid to the valve 210. In this case a tank 121' may be connected to the three-way valve 174 for collecting the chemical liquid, preferably as indicated in FIG. 4, through a valve 271.

The course of the measurement performed with the measuring system 300' according to FIG. 4 is very similar to that of the measuring system 300 depicted in FIG. 3.

The natural gas condensate and the stratum water and possibly any solid contaminants are preferably separated from the natural gas obtained from the gas pipeline before it is introduced into the gas conduit 110 through the valve 230. The pressure of the introduced natural gas is set by the pressure regulator 180, after which the examined inhibitor is fed into the gas conduit 110 with the inhibitor feeding system 142, as well as stratum water and natural gas condensate, in the proportions corresponding to that within the gas pipeline, with the stratum water feeding system 152 and the natural gas condensate feeding system 162. The mixture is delivered into the measuring cell 111' arranged in the heat exchange space 114 of the heat exchanger 112 where it is cooled by the cooling liquid within the heat exchange space 114. Any hydrate formation and its location are determined from the temperatures measured by the thermometers 140a, 140b, 140c and from the pressure differences measured by the differential pressure gauges 130a, 130b.

The natural gas, inhibitor, stratum water, natural gas condensate mixture, once it exits the measuring cell 111' is introduced into the separator 150 in order to separate the stratum water, natural gas condensate and solid contaminants. After this, the gas is led through the filter 199, then it passes the pressure regulator 190 and the choke valve 202 before it enters the flowmeter 204. The measurement data of the flowmeter 204 can also be used as an indicator of the possible presence of gas hydrates.

Figure 5A:
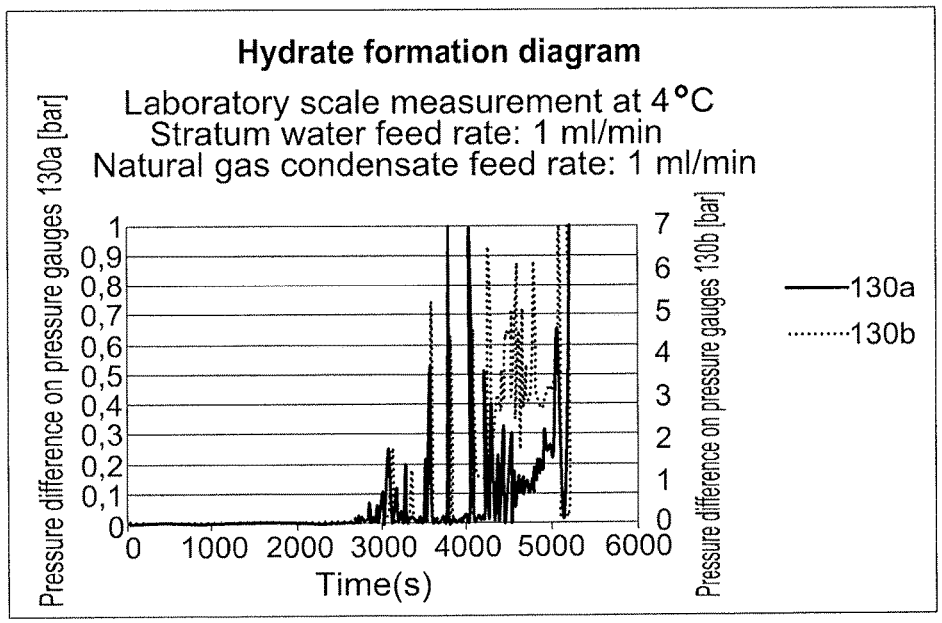
FIG. 5a is a pressure difference diagram obtained in a measurement performed by the measuring system according to FIG. 4.
Figure 5B:
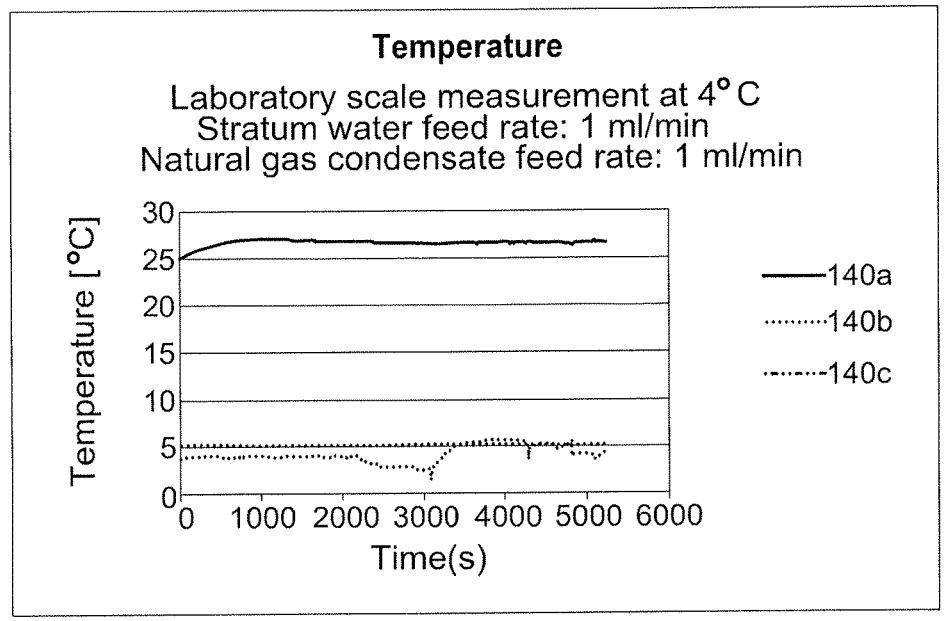
FIG. 5b is a temperature diagram obtained in a measurement performed by the measuring system according to FIG. 4.
Figure 5C:
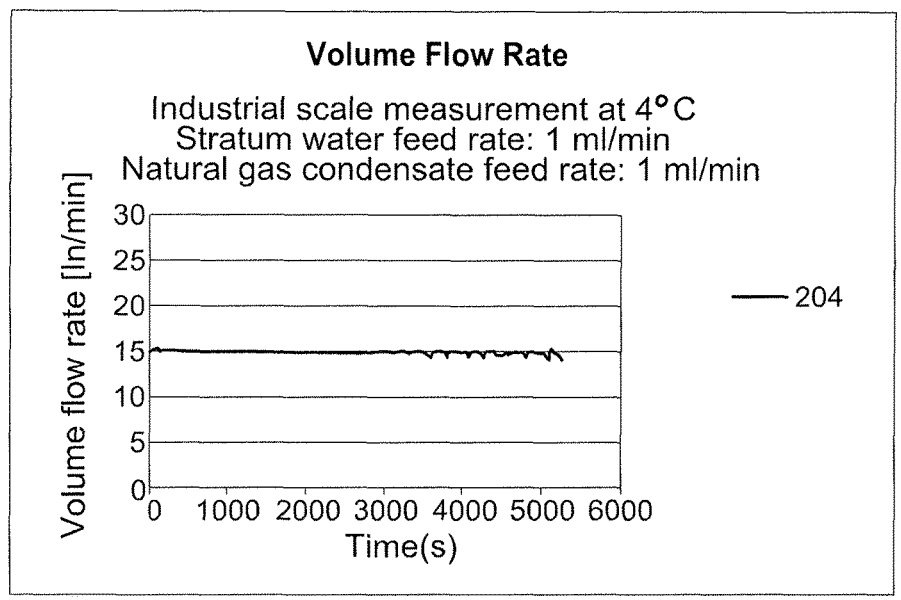
FIG. 5c is a volume flow rate diagram obtained in a measurement performed by the measuring system according to FIG. 4.

The measuring system 300' according to FIG. 4 has been built and the results of measurements performed with the measuring system 300' are shown in FIGS. 5a-5c and are discussed hereinafter.

Example 2

The length of the measuring cell 111' of the built measuring system 300' was 18 m, its inner diameter was 4 mm. The volume flow rate of the natural gas was set to 15 l/min with the help of the pressure regulator 190, which value was measured at normal atmospheric pressure. The gas was freed from stratum water, natural gas condensate and solid contaminants and into this gas stream stratum water was fed at a rate of 1 ml/min, and natural gas condensate was fed also at a rate of 1 ml/min by the stratum water feeding system 152 and the natural gas condensate feeding system 162, respectively. An inhibitor formed as the 1:1 ratio mixture of anti-agglomerate type GH-86 LDHI concentrate (sold by MOL-LUB Ltd., Hungary) and natural gas condensate was fed into the gas conduit 10 at a rate of 0.014 ml/min with the help of the feeding system 142.

The temperature of the cooling liquid within the heat exchange space 114 of the heat exchanger 112 was 4° C., which was continuously monitored by the thermometer 140'. The measurement performed with the laboratory scale measuring system 300' has the informative purpose of pre-screening the inhibitors, hence it is not an objective here to simulate the gas transport along the whole length of the gas pipeline. Accordingly, the measurement is performed for a shorter period of time. It has been found that it is practical to measure during 2 hours with the laboratory scale measuring system 300' as this is sufficient for pre-screening the given inhibitor. In the present case the measurement was only performed for a period of 5250 sec because by this time even the second differential pressure gauge 130b reached its upper measuring limit permanently.

The pressure differences measured by the differential pressure gauges 130a, 130b are plotted against time in FIG. 5a. As can be seen the differential pressure gauges 130a and 130b measured about 0 bar value during approx. 2500 sec, from whereon the measured values fluctuated strongly, meaning that the gas hydrate deposited on the inner wall of the measuring cell 111' was washed off by the gas stream repeatedly. After 3000 sec substantial pressure difference was observed by both differential pressure gauges 130a, 130b. After approx. 5000 sec both differential pressure gauges reached their upper measurement limit. From this it can be concluded that at a temperature of 4° C. after 2500 sec the supplied inhibitor is not sufficient anymore to prevent gas hydrate formation and the gas hydrate starts to deposit on the inner wall of the measuring cell 111', whereby the penetrable cross-section decreases and the pressure increases. It can also be concluded from the measurement data of the differential pressure gauges 130a, 130b that the gas hydrate formation also took place inside the first third of the measuring cell 111', because the first differential pressure gauge 130a measured substantial pressure difference as well. The sudden rise of pressure difference at approx. 5000 sec indicates the formation of a hydrate plug, the measuring cell 111' becomes highly impenetrable whereby the pressure difference drastically increases between the two sides of the hydrate plug.

The temperatures measured by the thermometers 140a, 140b, 140c are plotted against time in FIG. 5b. The first thermometer 140a measures the temperature at the inlet of the measuring cell 111' where the cooling liquid that is circulated in the heat exchange space 114 has not yet cooled the gas, thus this temperature is substantially higher. The second thermometer 140b is arranged at the third of the measuring cell 111', while the third thermometer 140c is arranged in the vicinity of the outlet. The third thermometer 140c should measure approximately the same but always somewhat lower temperature than the second thermometer 140b, however, as can be seen, after about 2000 sec the temperature measured by the third thermometer 140c starts to fluctuate, then rises after 3000 sec and surpasses the temperature measured by the second thermometer 140b. From this it can be concluded as well that after 3000 sec substantial hydrate formation occurs within the measuring cell 111'. It is further noted that in contrast to the arrangement of FIG. 4, in the real experiment the second thermometer 140b was arranged somewhat upstream of the second measuring point of the first differential pressure gauge 130a, thus it is presumed that the pressure difference indicated by the first differential pressure gauge 130a was caused by hydrate formation downstream of the second thermometer 140b.

FIG. 5c shows the volume flow rate measured by the flowmeter 204 and is plotted against time. The measurement data delivered by the flowmeter 204 also allows for deducting whether or not hydrate formation occurred because, due to the hydrate deposition, the volume flow rate of the gas temporarily decreases, then it is compensated, whereby the measured volume flow rate fluctuates in accordance with the pressure difference fluctuation after 3000 sec as can be seen in FIG. 5c.

Figure 6:
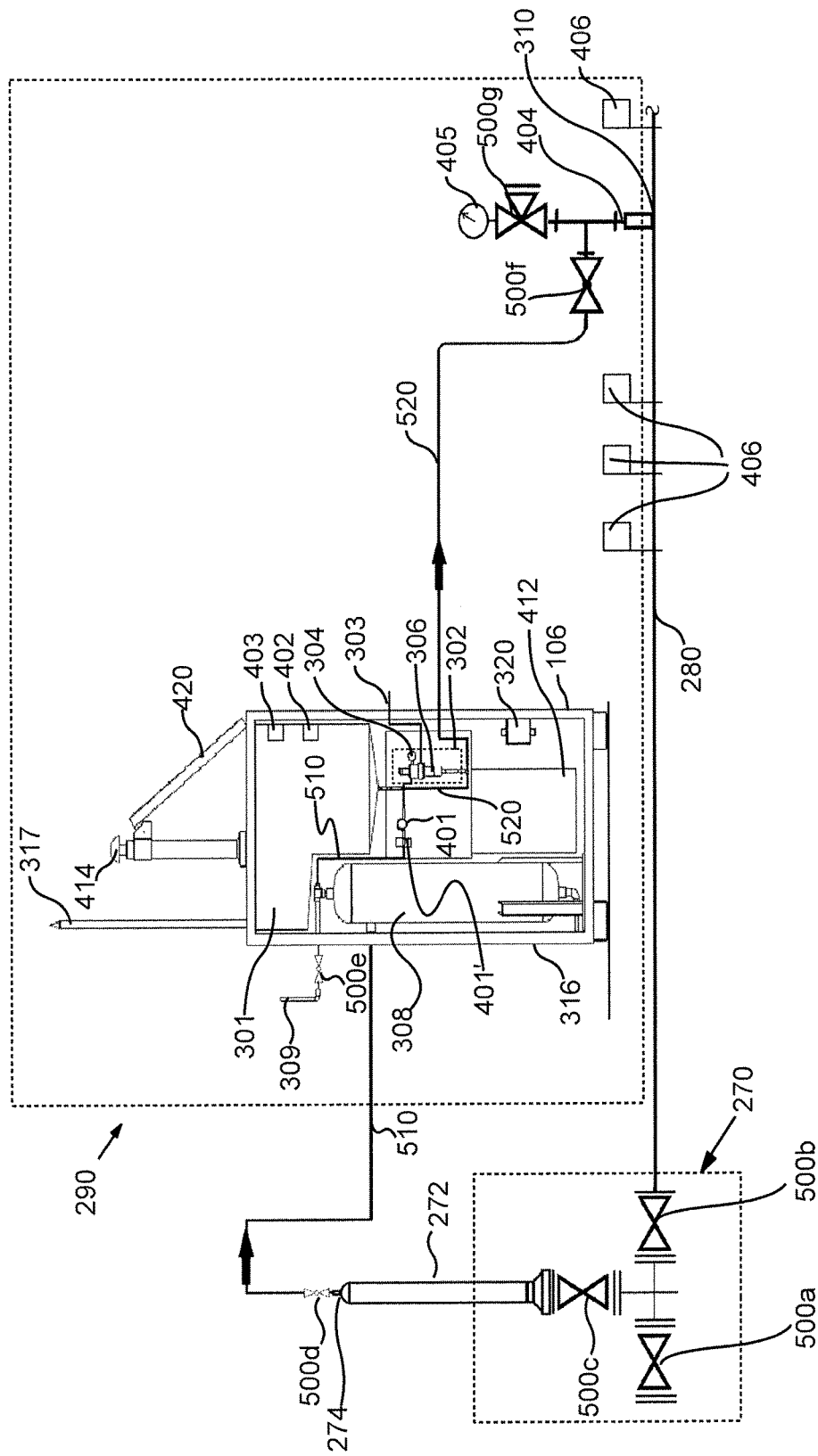
FIG. 6 is a schematic diagram of an inhibitor feeding system provided with telemetric data transmission for performing the process according to the invention.
Figure 7:
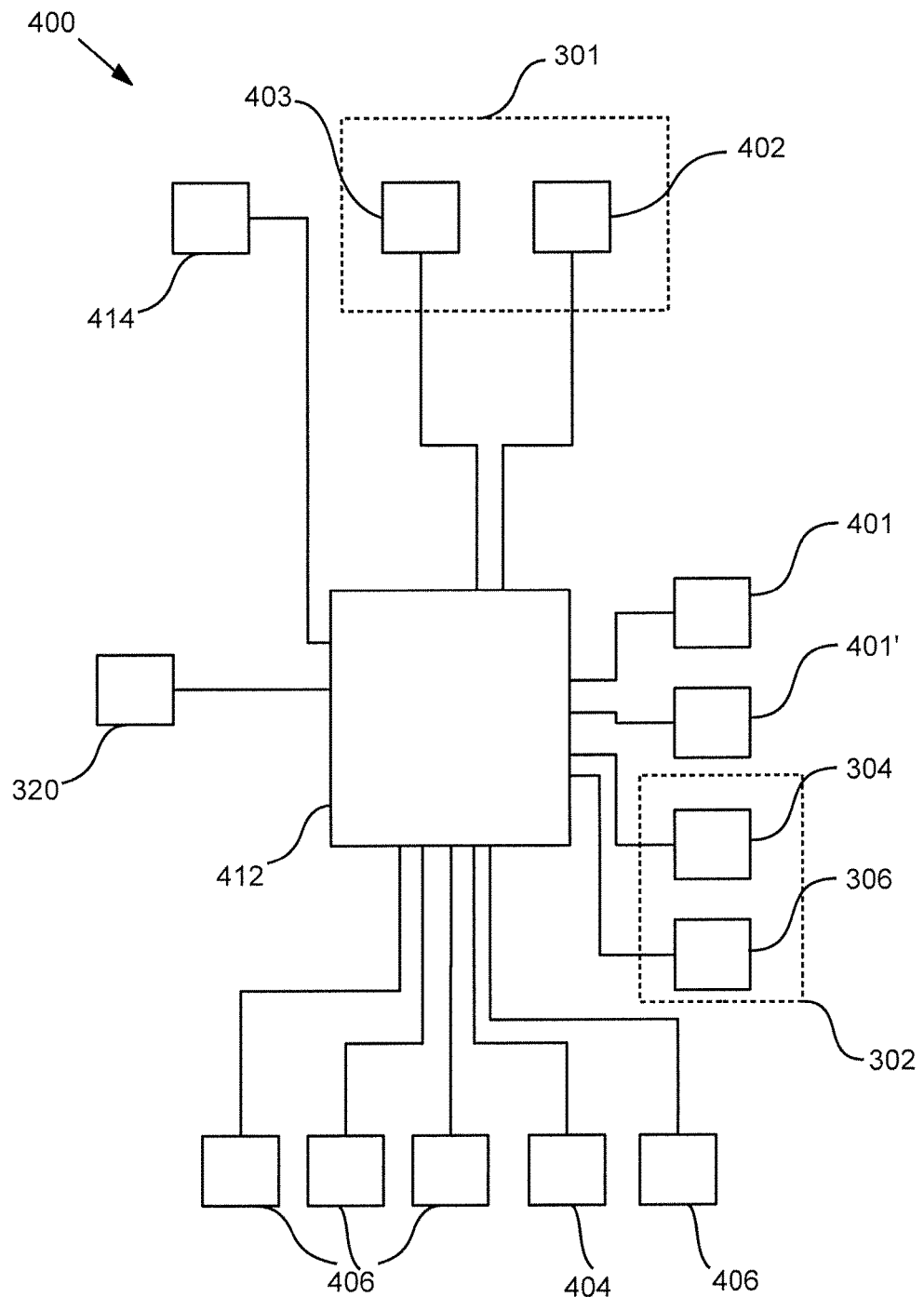
FIG. 7 is a schematic block diagram of a telemetric data transmission system of the inhibitor feeding system according to FIG. 6.

FIG. 6 illustrates a preferred embodiment of an inhibitor feeder 290 for carrying out the process according to the invention. The inhibitor feeder 290 provided for the process according to the invention comprises a telemetric data transmission system 400 (see FIG. 7) for remotely controlling and monitoring the inhibitor feeder 290. The inhibitor feeder 290 is connected to the gas well, preferably its well-head assembly 270 through a supply line 510 and is further connected through a feeding line 520 to a feeding point 310 of the gas pipeline 280 connected to the well-head assembly 270.

The telemetric data transmission system 400 comprises hardware and software components, which allow for transmitting measurement data of measuring devices of the telemetric data transmission system 400 to a remote center through an electronic communication channel.

Electronic communication channel may be established for example within the framework of an electronic communication network, which can be a wired and/or wireless local area IT network (LAN) or a global IT network, in particular the Internet, furthermore a mobile telecommunication network employing e.g. 3G or 4G communication protocols, GSM network, satellite communication network, etc.

The remote center may be a dispatcher center or a server comprising programs, which when executed automatically monitor and control the inhibitor feeder 290.

According to a preferred embodiment the telemetric data transmission system 400 comprises an energy supply system 320 for providing the current supply necessary for its operation. The energy supply system 320 may be a current generator, fuel cell or e.g. accumulator. According to a particularly preferred embodiment the energy supply system 320 comprises one or more solar cells 321 arranged on top of and/or beside the inhibitor feeder 290. In case of appropriate weather conditions the telemetric data transmission system 400 may be supplied with energy for its operation directly by the solar cells 321, or, as the case may be, the electric energy generated by the solar cells 321 may be used for charging accumulators of the energy supply system 320.

The inhibitor feeder 290 preferably comprises a tank 301 for storing the inhibitor, and comprises a pump 302 connected therewith through the feeding line 520 for delivering the inhibitor into the gas pipeline 280 from the tank 301. The inhibitor feeder 290 can be used to feed an inhibitor concentrate or, as the case may be, an inhibitor formed as the mixture of an inhibitor concentrate and an appropriate solvent (e.g. natural gas condensate, methanol).

According to a preferred embodiment the pump 302 is a pneumatic pump comprising a piston which is actuated by the gas supplied from the gas well through the supply line 510, and a remote-controlled stroke rate regulator 304 regulating the stroke count per minute of the piston. The pneumatic pump 302 is preferably provided with an exhaust vent 303. Other embodiments are also conceivable, wherein the pump 302 is not actuated by the gas pressure but instead by an electric motor. In such a case the energy supply of the electric motor is preferably ensured by the energy supply system 320 and/or the solar cells 321.

In case of the pneumatic pump 302 the feed rate of the inhibitor can be set by regulating the stroke count per minute of the piston and/or the stroke length of the piston. According to a particularly advantageous embodiment the pneumatic pump 302 comprises a remote-controlled stroke length regulator 306 for regulating the stroke length of the piston.

The energy required for the operation of the pneumatic pump 302 is preferably ensured by the pressure of the gas coming from the gas well. The supply line 510 of the inhibitor feeder 290 is preferably connected to the well head, preferably to an upper sample outlet 274 of a conduit branch 272 mounted on the well-head assembly (Christmas-tree) 270 in order to obtain preferably dry, liquid-phase free gas from the highest point of the conduit branch 272.

According to a preferred embodiment a separator 308 is connected to the supply line 510 upstream of the pump 302 for separating the liquid phase and, as the case may be, solid contaminants from the gas obtained from the gas well before the gas is introduced into the pneumatic pump 302, whereby the lifetime of the pump 302 can be increased and the risk of breakdown reduced. The separator 308 may be substantially the same type as the above-disclosed separators 50, 50', comprising a tank preferably filled with glycol through which the gas is blown through in order to dry it. The glycol bonds most of the liquid and contaminants carried by the gas, however, it is further possible to include one or more filters between the separator 308 and the pneumatic pump 302 in order to filter out any eventual contaminants that remained in the gas after having passed the separator 308, whereby the gas can be further cleaned. The separator 308 preferably comprises a blow-off vent 309 through which the high pressure gas can be discharged from the separator 308 in case of maintenance.

According to a preferred embodiment the telemetric data transmission system 400 of the inhibitor feeder 290 comprises one or more measuring devices, for example a pressure gauge 401 connected to the supply line 510, a liquid-level meter 402 arranged within the tank 301 and optionally a thermometer 403, as well as a flowmeter 404 and a pressure gauge 405 the latter two being connected to the feeding line 520 connecting the inhibitor feeder 290 with the feeding point 310, or these can form part of the assembly installed at the feeding point 310. The telemetric data transmission system 400 further comprises one or more ground thermometers 406 (soil thermometers), which are arranged along the gas pipeline 280. One or more physical parameters of the inhibitor feeder 290 and the environment is measured with the help of the measuring devices, such parameters may be the quantity of the inhibitor within the tank 301 and/or the temperature of the inhibitor within the tank 301 and/or the pressure at the feeding point 310, and/or the pressure of the gas actuating the pneumatic pump 302 and/or the amount of inhibitor flowing through the feeding point 310 and/or the temperature of the environment surrounding the gas pipeline 280.

The ground thermometers 406 are preferably installed below the ground level, in the vicinity of the gas pipeline 280, whereby the local temperature of the transported gas can be estimated with good approximation. The ground thermometers 406 are preferably installed along the gas pipeline 280 upstream and downstream of the feeding point 310 at regular equal intervals or, as the case may be, at other given distances from each other.

According to a preferred embodiment the telemetric data transmission system 400 comprises a control unit 412 for collecting and storing the measurement data provided by the measuring devices of the telemetric data transmission system 400 and for controlling the pneumatic pump 302.

The control unit 412 may be a computer, microcontroller or any other hardware device, which is suitable for storing and preferably for processing the data measured by the telemetric data transmission system 400. The control unit 412 preferably comprises one or more input devices (for example a keyboard—not shown), one or more output devices (for example a display—not shown), and may also comprise an interface serving both as input and output device (for example a touchscreen—not shown). Preferably a communication module 414 is connected to the control unit 412 with which the measurement data may be transmitted to a remote center, e.g. a server, over a wired or wireless electronic communication channel. According to a preferred embodiment the communication module 414 may comprise a parabolic antenna suitable for satellite data transmission and the measurement data is transmitted to the remote center over a satellite communication channel. This embodiment can be particularly advantageous in such cases for example when the inhibitor feeder 290 is installed at a site (e.g. desert), where there is no conventional wired or wireless communication network.

The control unit 412 is in wired or wireless connection with the stroke rate regulator 304 and the stroke length regulator 306 of the pneumatic pump 302. The wired communication may apply RS485 standard, wireless connection can be ensured for example by applying Bluetooth or ZigBee protocols as is known to a person of ordinary skill in the art. The control unit 412 preferably stores the data received from the measuring devices.

The inhibitor feeder 290 is connected to the well-head assembly 270 and to the gas pipeline 280 by regulators 500a, 500b and 500c. In the context of the present invention the regulator 500a, 500b, 500c means a device which is suitable for regulating flow inside a pipe. The regulator 500a, 500b, 500c, 500d may be e.g. a valve, a tap or a gate valve. Regulators 500e, 500f, 500g may also be provided between the components of the inhibitor feeder 290 for regulating the flow.

According to a particularly preferred embodiment the inhibitor feeder 290 (with the exception of certain measuring devices) may be arranged inside a metal container 316 having solid walls and lockable door. The container 316 has for function to protect the inhibitor feeder 290 installed at the gas well from environmental conditions (e.g. weather), and to prevent unauthorized persons from accessing the inhibitor feeder 290. Preferably, a motion detection sensor (e.g. reed relay, Hall-sensor, etc.) connected to the control unit 412 is arranged at the door of the container 316, with the help of which the opening and closing of the door can be monitored from the remote center. According to a preferred embodiment the container 316 comprises a lightning guard 317 made of an electrically conducting, mechanically strong material, for example of steel. One end of the lightning guard 317 is arranged on the top of the container 316, while the other end is buried in the ground as is known to a person of ordinary skill in the art.

In the following, the use of the inhibitor feeder 290 will be explained.

The inhibitor is fed into the gas pipeline 280 through the feeding point 310 by the inhibitor feeder 290 equipped with the telemetric data transmission system 400 at a rate determined with the help of the measuring system 100.

In a first step of the inhibitor feeding process gas is extracted from the well-head assembly 270, from which the liquid phase (practically the stratum water and the natural gas condensate) as well as the solid contaminants are separated with the help of the separator 308. The cleaned dry gas is then introduced from the separator 308 into the pneumatic pump 302 through the supply line 510. According to a preferred embodiment the pressure of the gas supplied to the pneumatic pump 302 is regulated with the help of the pressure regulator 401'. In a given case it is also conceivable to equip the supply line 510 with a regulating valve (not shown), for example a ball valve with which the supply line 510 can be closed-off.

The quantity of the gas reaching the piston of the pneumatic pump 302 is set with the help of the stroke rate regulator 304. The stroke rate regulator 304 functions as a valve, which permits the flow of a given quantity of gas at given time intervals. The piston of the pneumatic pump 302 is driven by the dry gas, which is allowed to flow through the stroke rate regulator 304. The gas driving the pneumatic pump 302 exits through the exhaust vent 303. The inlet of the pneumatic pump 302 is connected to the inhibitor tank 301 through the feeding line 520, and its outlet is connected to the feeding point 310 through the feeding line 520. According to a particularly preferred embodiment the stroke rate regulator 304 is connected to the control unit 412 through wired or wireless connection. The stroke rate regulator 304 is controlled from the remote center through the control unit 412 with the help of the telemetric data transmission system 400. Data is received from the remote center with the help of the communication module 414, and the received data is forwarded to the control unit 412. The control unit 412 preferably processes the received data and carries out the controlling of the stroke rate regulator 304.

The quantity of the inhibitor that is delivered by the pneumatic pump 302 depends on the one hand on the stroke count per minute of the piston, and on the other hand on its stroke length. According to a preferred embodiment the feeding rate of the inhibitor introduced into the gas pipeline 280 is set to the desired value during the remote control of the inhibitor feeder 290 by remotely controlling the stroke rate regulator 304 to set the stroke count per minute of the piston. By regulating the stroke length of the piston it is possible to set the quantity of the inhibitor that is delivered by the pneumatic pump 302 even more accurately. Since in certain cases the inhibitor is supplied in only a few ml/min feed rate into the gas pipeline 280, thus, according to a particularly preferred embodiment, the stroke length of the piston is also controlled from the remote center with the help of the stroke length regulator 306 in order to more accurately control the inhibitor feeding. According to this embodiment the stroke length regulator 306 is also connected to the control unit 412 and the remote control is accomplished as explained in connection with the stroke rate regulator 304. Naturally, as the case may be, the stroke length and stroke count per minute of the piston, and thereby the quantity of the inhibitor delivered by the pump 302, may be set manually on-site.

According to a preferred embodiment of the inventive process the telemetric data transmission system 400 also comprises the thermometer 403 and the liquid-level meter 402 connected to the tank 301, which allow for measuring the inhibitor level and the temperature within the tank 301. The measurement data of the thermometer 402 and of the liquid-level meter 402 are preferably transmitted to the control unit 412 over wired or wireless connection.

By remotely monitoring the inhibitor level and the temperature within the tank 301 it is possible to prevent or to rapidly eliminate breakdown due to any technical defect (such as defect of the tank 301, leakage, stoppage, etc.), furthermore the continuous, undisturbed operation of the inhibitor feeder 290 can be ensured. If the measurement data shows that more inhibitor is released from the tank 301 than the quantity delivered by the pneumatic pump 302, then it can be deduced that the tank 301 is leaking and maintenance workers may be sent from the remote center to the inhibitor feeder 290.

According to a preferred embodiment the telemetric data transmission system 400 comprises further measuring devices, such as the pressure gauge 405 and the flowmeter 404 installed at the feeding point 310. A pressure regulator 401' may be installed between the separator 308 and the pressure gauge 401 in order to reduce the pressure of the gas transported inside the supply line 510. The physical parameters measured by the above-indicated measuring devices are preferably also sent to the remote center. For example, based on the data sent from the pressure gauge 405 and the flowmeter 404 installed at the feeding point 310, any leakage or stoppage of the feeding line 520, 520 may be observed, and by monitoring the pressure of the gas driving the pneumatic pump 302 breakdown of the pneumatic pump 302 can be observed. In case of any breakdown is observed maintenance workers may be sent from the remote center to the inhibitor feeder 290.

According to a particularly preferred embodiment of the telemetric data transmission system 400 comprises one or more ground thermometers 406, which are in wireless connection with the control unit 412 as discussed above.

According to a preferred embodiment of the inventive process the temperature of the gas pipeline 280 is measured at one or more locations by the one or more ground thermometers 406 and the measurement data is transmitted to the remote center by the telemetric data transmission system 400. The feeding rate of the inhibitor is then corrected with regard to the measured temperatures. For example if the temperature of the gas pipeline 280 and thereby that of the transported gas decreases due to a substantial cooling of the environment, then the feeding rate of the inhibitor is increased in response of the received temperature data by the remote center with the help of the telemetric data transmission system 400 without the need to personally visit the inhibitor feeder 290.

The invention has for advantage that the remote monitoring of the inhibitor feeder 290 and the gas pipeline 280 with the help of the telemetric data transmission system 400 allows for faster observation of any breakdown or environmental change, and consequently for faster reaction. A further advantage of the invention is that the inhibitor feeder 290 can be controlled remotely, thus the feeding rate of the inhibitor can be controlled remotely in accordance with the received measurement data (e.g. temperature of the gas pipeline 280) without field work.

Various modifications to the above disclosed embodiments will be apparent to a person skilled in the art without departing from the scope of protection determined by the attached claims.

What is claimed:

1. Examination process for replicating hydrate forming conditions in a gas pipeline and monitoring the effect of a low dosage hydrate inhibitor (LDHI) in suppressing hydrate formation at temperatures and pressures encountered in gas pipelines for dynamically determining LDHI feed rate for inhibition of hydrate formation comprising the steps of:
diverting from a gas well a sample gas stream at a preselected rate;
introducing the diverted gas stream into a gas conduit through an inlet of the gas conduit;
feeding LDHI into the diverted gas stream at one or more predetermined rates to produce a LDHI-containing gas stream;
introducing the LDHI-containing gas stream into a coolable portion of the gas conduit at a predetermined pressure, which coolable portion is provided with pressure sensors along the coolable portion;
cooling the LDHI-containing gas stream passing through the coolable portion of the gas conduit by cooling the coolable portion to a predetermined temperature; and
monitoring pressure of the LDHI-containing gas stream passing through the coolable portion of the gas conduit for a predetermined time period;
whereby a substantially uniform pressure drop along the coolable portion of the gas conduit during the predetermined time period indicates a LDHI feed rate sufficient to suppress hydrate formation at the predetermined temperature.

2. The process according to claim 1, characterized by performing the examination of the hydrate formation for a LDHI delivered at least at two different feeding rates and/or for at least two types of LDHIs and/or at least at two given temperatures.

3. The process according to claim 1, characterized by that the predetermined observation time is at least twice the gas residence time within the gas pipeline.

4. The process according to claim 1, characterized by providing a coil pipe as the coolable portion of the gas conduit, the coil pipe having an inner diameter of at least 7 mm, more preferably of at least 10 mm and having a length of at least 100 m, preferably not more than 200 m.

5. The process according to claim 1, characterized by washing the coolable portion of the gas conduit with hot water and blowing air or nitrogen there through between consecutive measurements.

6. The process according to claim 1, characterized by providing temperature sensors along the coolable portion of the gas conduit and measuring the temperature of the coolable portion in at least two locations, whereby a substantially uniform temperature along the coolable portion of the gas conduit during the predetermined time range indicates a LDHI feed rate sufficient to suppress hydrate formation.

7. The process according to claim 1, characterized by separating the liquid phase and solid contaminants from the gas with a separator prior to feeding the LDHI into the gas conduit.

8. The process according to claim 1, characterized by determining the quantity of stratum water and natural gas condensate carried in the gas pipeline, and after having separated the liquid phase feeding stratum water and natural gas condensate to the gas inside the gas conduit in accordance with the determined quantities prior to introducing the gas into the coolable portion.

9. The process according to claim 1, characterized by cooling the coolable portion by introducing a cooling medium into a heat exchange space of a heat exchanger and in case of hydrate formation discharging the cooling medium into a tank, and heating the coolable portion by an air heater connected to the heat exchange space until the hydrate plug is eliminated.

10. The process according to claim 1, characterized by setting a desired mass flow of the gas inside the gas conduit by a choke valve connected to the gas conduit.

11. The process according to claim 1, characterized by performing a pre-measurement in a laboratory scale measuring system for pre-screening the LDHIs that are to be examined, by:
taking gas sample from a gas well,
introducing the gas sample into a gas conduit of the laboratory scale measuring system,
feeding LDHI that is to be pre-screened into the gas conduit of the laboratory scale measuring system to produce a LDHI-containing gas sample,
introducing the LDHI-containing gas sample into a maximum 20 m long coolable portion of the gas conduit of the laboratory scale measuring system, which coolable portion is provided with pressure sensors along the coolable portion;

cooling the LDHI-containing gas sample passing through the coolable portion of the gas conduit of the laboratory scale measuring system by cooling said coolable portion to a predetermined temperature; and monitoring pressure of the LDHI-containing gas sample passing through the coolable portion of the gas conduit of the laboratory scale measuring system;

whereby a substantially uniform pressure drop along the coolable portion of the gas conduit during of the laboratory scale measuring system indicates a LDHI feed rate sufficient to suppress hydrate formation in the gas sample.

12. The process according to claim 11, characterized by providing a measuring cell as the coolable portion of the gas conduit of the laboratory scale measuring system, the measuring cell having an inner diameter of 3 to 5 mm, preferably of about 4 mm.

13. The process according to claim 11, characterized by performing the examination of the hydrate formation in the laboratory scale measuring system for an LDHI added in various different quantities and/or at least two types of LDHIs and/or at least at two given temperatures.

14. The process according to claim 13, characterized by washing the coolable portion of the gas conduit of the laboratory scale measuring system with hot water and blowing air there through between consecutive measurements.

15. The process according to claim 11, characterized by separating the liquid phase and eventually solid contaminants from the gas taken from the gas well with a separator.

16. The process according to claim 11, characterized by determining the amount of stratum water and natural gas condensate carried in the gas pipeline, and after having separated the liquid phase, feeding stratum water and natural gas condensate into the gas in accordance with the determined amounts prior to introducing the gas into the coolable portion of the laboratory scale measuring system.

17. The process according to claim 11, characterized by taking the gas from a gas inlet of the gas conduit of the laboratory scale measuring system, which gas conduit is connectable to a well-head of the gas well for the purpose of pre-measurement.

18. The process according to claim 11, characterized by introducing the gas from the gas well into a gas bottle and feeding the gas into the gas of the laboratory scale measuring system conduit therefrom for the purpose of pre-measurement.

19. The process according to claim 1, characterized by providing an LDHI feeder comprising a telemetric data transmission system for the remote control and monitoring of the LDHI feeder, and connecting the LDHI feeder to a feeding point of the gas pipeline, determining a temperature of the gas pipeline, and feeding the LDHI into the gas pipeline through the feeding point by the LDHI feeder at a LDHI feed rate sufficient to suppress hydrate formation at a temperature not exceeding the gas pipeline temperature.

20. The process according to claim 19, characterized by that the LDHI feeder comprises a tank for storing the LDHI, a pump for delivering the LDHI from the tank into the gas pipeline and during the remote monitoring of the LDHI feeder by the telemetric data transmission system measuring, via measuring devices, the quantity of the LDHI within the tank and/or the temperature of the LDHI within the tank and/or the pressure at a well head of the gas well and/or the pressure at the feeding point and/or the pressure of the gas actuating the pump and/or the flow rate of the LDHI flowing through the feeding point, and transmitting the measured data to a remote center.

21. The process according to claim 19, characterized by that the telemetric data transmission system comprises a control unit, and by collecting and storing the data measured by the measuring devices of the telemetric data transmission system, and controlling the pump by the control unit.

22. The process according to claim 19, characterized by determining the temperature of the gas pipeline by measuring the temperature of the gas pipeline at least at one location and transmitting the measured data to a remote center by the telemetric data transmission system.

23. The process according to claim 22, characterized by adjusting the feed rate of the LDHI with regard to the measured temperatures.

24. The process according to claim 20, characterized by that the pump comprises a piston and a remotely controllable stroke rate regulator for regulating the stroke rate of the piston, and by controlling the stroke rate of the piston from the remote center in the course of the remote control of the LDHI feeder.

25. The process according to claim 20, characterized by that the pump comprises a piston and a remotely controllable stroke length regulator for regulating the stroke length of the piston, and by controlling the stroke length of the piston from the remote center in the course of the remote control of the LDHI feeder.

26. The process according to claim 20, characterized by that the LDHI feeder comprises as the pump a pneumatic pump actuated by gas obtained from the gas well, and by separating liquid phase and in a given case solid contaminants by a separator from the gas actuating the pneumatic pump that is obtained from the gas well before introducing the gas into the pneumatic pump.

27. The process according to claim 19, characterized by providing the telemetric data transmission system with an energy supply system for current supply necessary for its operation, which preferably comprises an accumulator and/or fuel cell and/or solar cell.

28. The process according to claim 19, characterized by arranging the LDHI feeder in a container having solid walls.

* * * * *